(12) United States Patent
Konno et al.

(10) Patent No.: US 11,103,348 B2
(45) Date of Patent: Aug. 31, 2021

(54) METHOD FOR CONVERTING AN ANNULOPLASTY RING IN VIVO

(71) Applicant: Edwards Lifesciences Corporation, Irvine, CA (US)

(72) Inventors: Mark A. Konno, Laguna Beach, CA (US); Yaron Keidar, Kiryat Ono (IL)

(73) Assignee: Edwards Lifesciences Corporation, Irvine, CA (US)

(*) Notice: Subject to any disclaimer, the term of this patent is extended or adjusted under 35 U.S.C. 154(b) by 98 days.

(21) Appl. No.: 16/600,362

(22) Filed: Oct. 11, 2019

(65) Prior Publication Data
US 2020/0038185 A1  Feb. 6, 2020

Related U.S. Application Data

(60) Division of application No. 15/498,213, filed on Apr. 26, 2017, now Pat. No. 10,478,301, which is a continuation of application No. 14/038,357, filed on Sep. 26, 2013, now Pat. No. 9,636,219, which is a continuation of application No. 12/234,559, filed on Sep. 19, 2008, now Pat. No. 9,314,335.

(51) Int. Cl.
*A61F 2/24* (2006.01)
*A61F 2/958* (2013.01)

(52) U.S. Cl.
CPC .......... *A61F 2/2442* (2013.01); *A61F 2/2409* (2013.01); *A61F 2/2412* (2013.01); *A61F 2/2418* (2013.01); *A61F 2/2433* (2013.01); *A61F 2/2445* (2013.01); *A61F 2/2427* (2013.01); *A61F 2/958* (2013.01); *A61F 2220/0075* (2013.01); *A61F 2230/0034* (2013.01); *A61F 2250/001* (2013.01); *A61F 2250/0071* (2013.01)

(58) Field of Classification Search
CPC .................................. A61F 2/24; A61F 2/2442
See application file for complete search history.

(56) References Cited

U.S. PATENT DOCUMENTS

| 3,656,185 A | 4/1972 | Carpentier |
| 4,055,861 A | 11/1977 | Carpentier et al. |
| 4,164,046 A | 8/1979 | Cooley |

(Continued)

FOREIGN PATENT DOCUMENTS

| EP | 0338994 A1 | 10/1989 |
| EP | 1034753 A1 | 9/2000 |

(Continued)

*Primary Examiner* — Matthew W Schall
(74) *Attorney, Agent, or Firm* — Guy Cumberbatch

(57) ABSTRACT

The invention is a cardiac implant, and associated methods therefore, configured to repair and/or replace a native heart valve, and having a support frame configured to be reshaped into an expanded/changed form in order to receive and/or support an expandable prosthetic heart valve therein. The implant may be configured to have a generally rigid and/or expansion-resistant configuration when initially implanted to replace/repair a native valve (or other prosthetic heart valve), but to assume a generally non-rigid and/or expanded/expandable form when subjected to an outward force such as that provided by a dilation balloon. The implant may be configured to have a generally D-shaped configuration when initially implanted, but to assume a generally circular form when subjected to an outward force such as that provided by a dilation balloon.

23 Claims, 19 Drawing Sheets

(56) References Cited

U.S. PATENT DOCUMENTS

| | | |
|---|---|---|
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,348,068 B1 | 2/2002 | Campbell et al. |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,524,330 B2 | 4/2009 | Berreklouw |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,780,723 B2 | 8/2010 | Taylor |
| 7,806,927 B2 | 10/2010 | Styrc |
| 7,871,436 B2 | 1/2011 | Ryan et al. |
| 8,226,707 B2 | 7/2012 | White |
| 8,246,677 B2 | 8/2012 | Ryan |
| 8,496,700 B2 | 7/2013 | Edoga et al. |
| 8,500,802 B2 | 8/2013 | Lane et al. |
| 2001/0021874 A1 | 9/2001 | Carpentier et al. |
| 2002/0062150 A1 | 5/2002 | Campbell et al. |
| 2003/0033009 A1 | 2/2003 | Gabbay |
| 2003/0040793 A1 | 2/2003 | Marquez |
| 2003/0199971 A1 | 10/2003 | Tower et al. |
| 2004/0210305 A1 | 10/2004 | Shu et al. |
| 2004/0249452 A1 | 12/2004 | Adams et al. |
| 2004/0249453 A1 | 12/2004 | Cartledge et al. |
| 2005/0096739 A1 | 5/2005 | Cao |
| 2005/0131533 A1 | 6/2005 | Alfieri et al. |
| 2005/0240200 A1 | 10/2005 | Bergheim |
| 2005/0251251 A1 | 11/2005 | Cribier |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2006/0052867 A1 | 3/2006 | Revuelta et al. |
| 2007/0016287 A1 | 1/2007 | Cartledge et al. |
| 2007/0067029 A1 | 3/2007 | Gabbay |
| 2007/0100441 A1 | 5/2007 | Kron et al. |
| 2007/0142907 A1 | 6/2007 | Moaddeb et al. |
| 2007/0162111 A1 | 7/2007 | Fukamachi et al. |
| 2007/0244546 A1 | 10/2007 | Francis |
| 2008/0027483 A1 | 1/2008 | Cartledge et al. |
| 2008/0114452 A1 | 5/2008 | Gabbay |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Lobbi |
| 2008/0275549 A1 | 11/2008 | Rowe |
| 2009/0005863 A1 | 1/2009 | Goetz et al. |
| 2009/0082857 A1 | 3/2009 | Lashinski et al. |
| 2009/0093876 A1 | 4/2009 | Nitzan et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192606 A1 | 7/2009 | Gloss et al. |
| 2009/0216322 A1 | 8/2009 | Le et al. |
| 2009/0281609 A1 | 11/2009 | Benichou et al. |
| 2010/0076548 A1 | 3/2010 | Konno |
| 2010/0076549 A1 | 3/2010 | Keidar et al. |
| 2011/0166636 A1 | 7/2011 | Rowe |
| 2011/0178597 A9 | 7/2011 | Navia et al. |
| 2011/0264207 A1 | 10/2011 | Bonhoeffer et al. |

FOREIGN PATENT DOCUMENTS

| | | |
|---|---|---|
| EP | 1755459 A2 | 2/2007 |
| EP | 1804726 A1 | 7/2007 |
| EP | 1958598 A1 | 8/2008 |

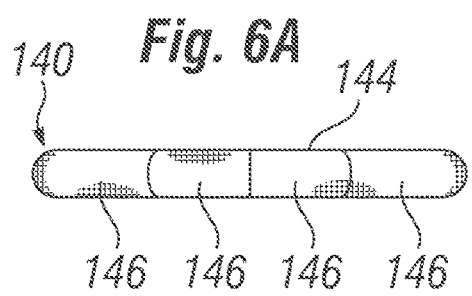
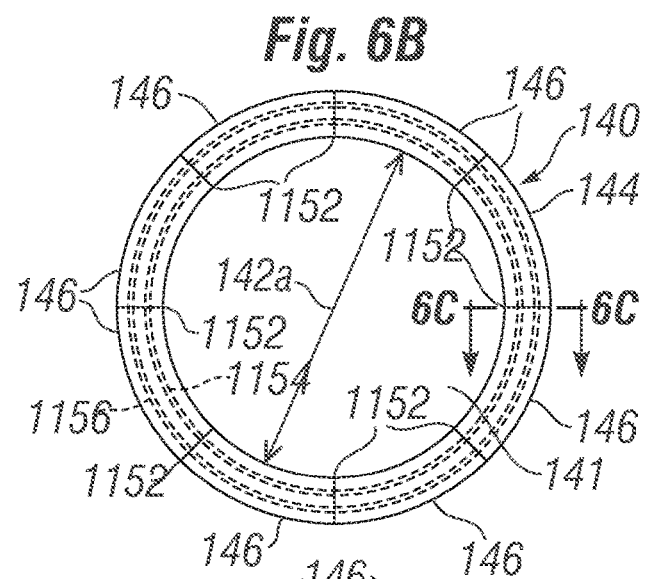
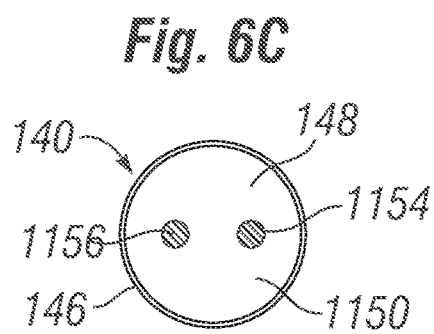
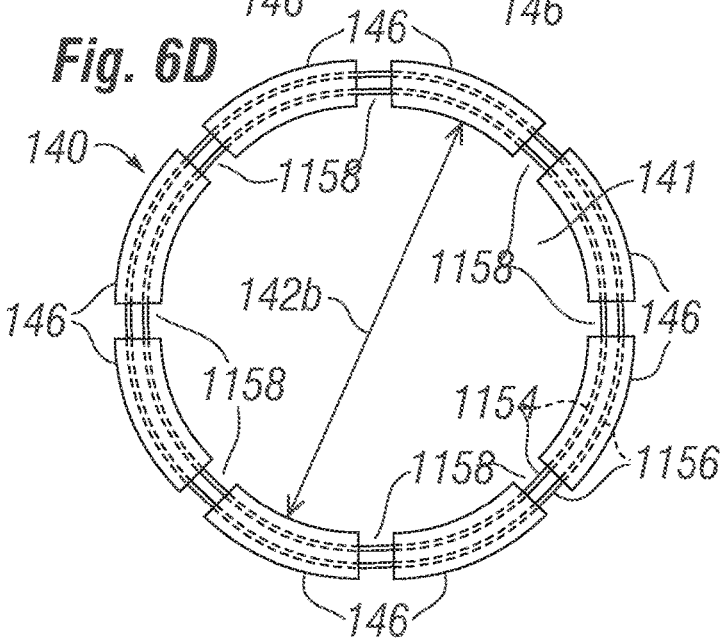

Fig. 8A
Fig. 9A

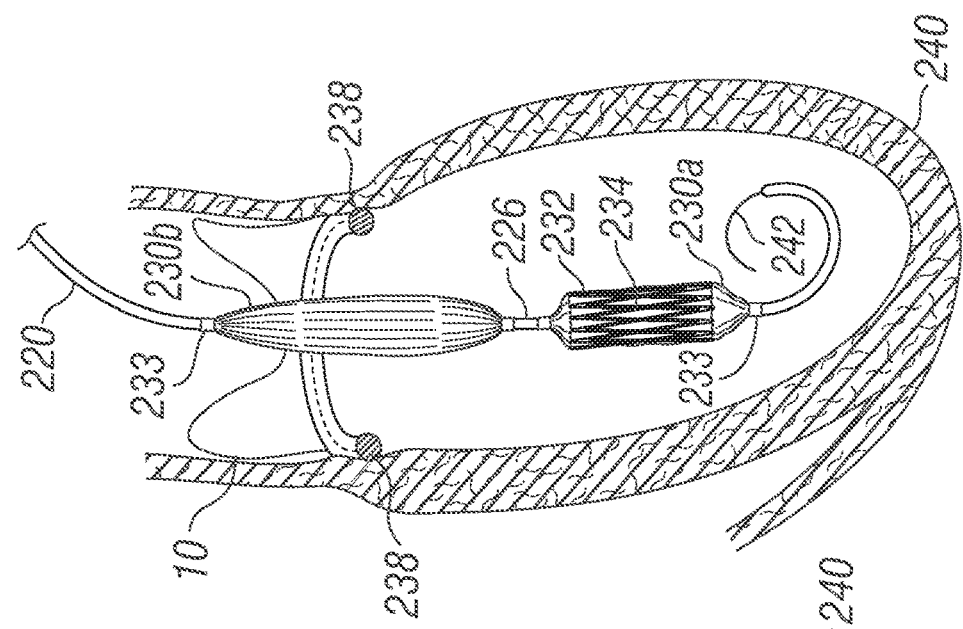
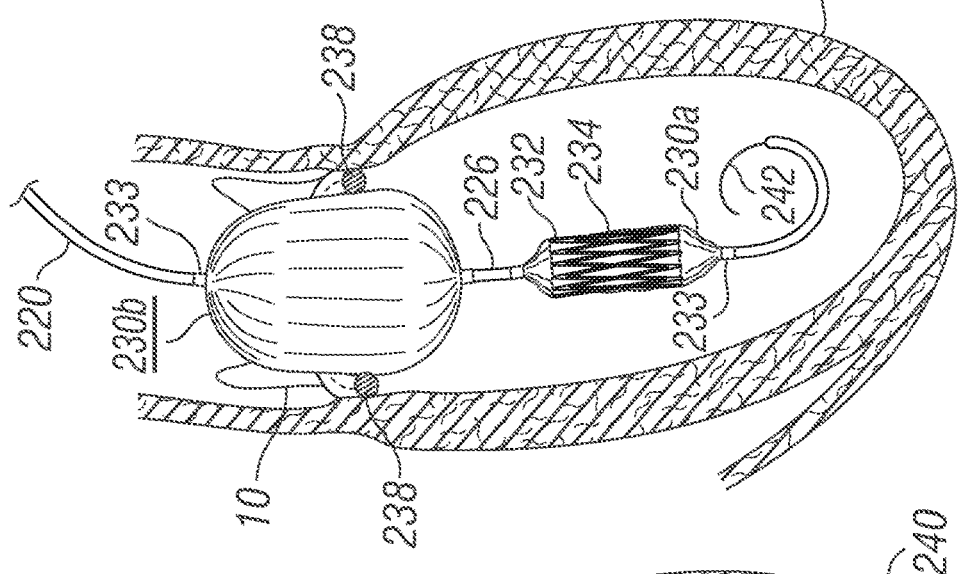
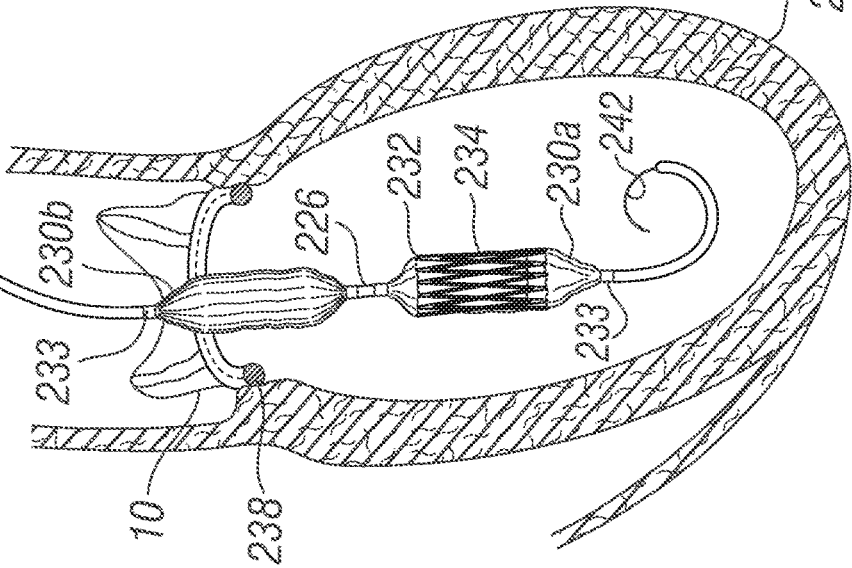

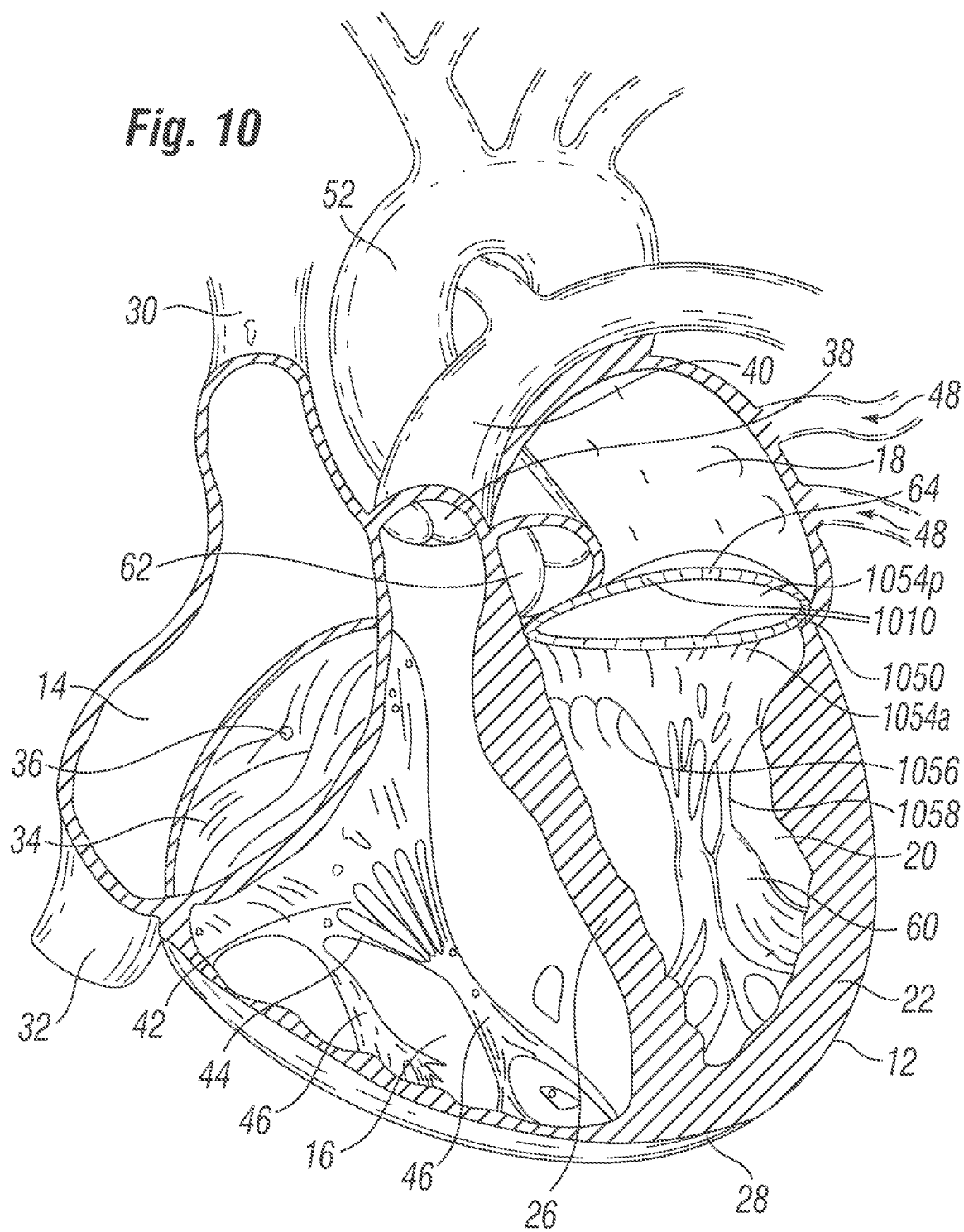

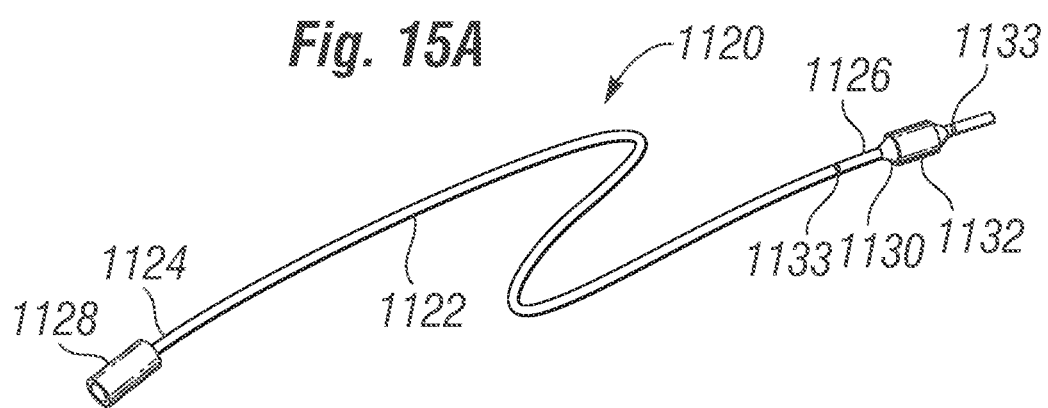
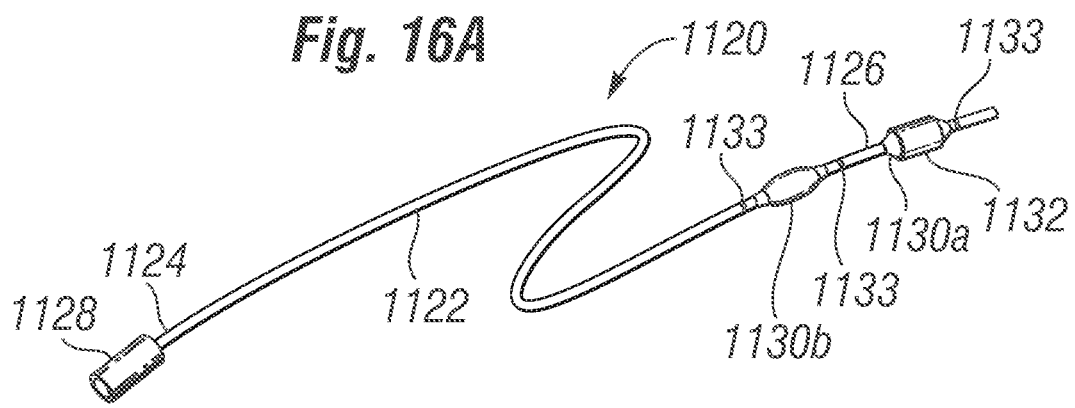

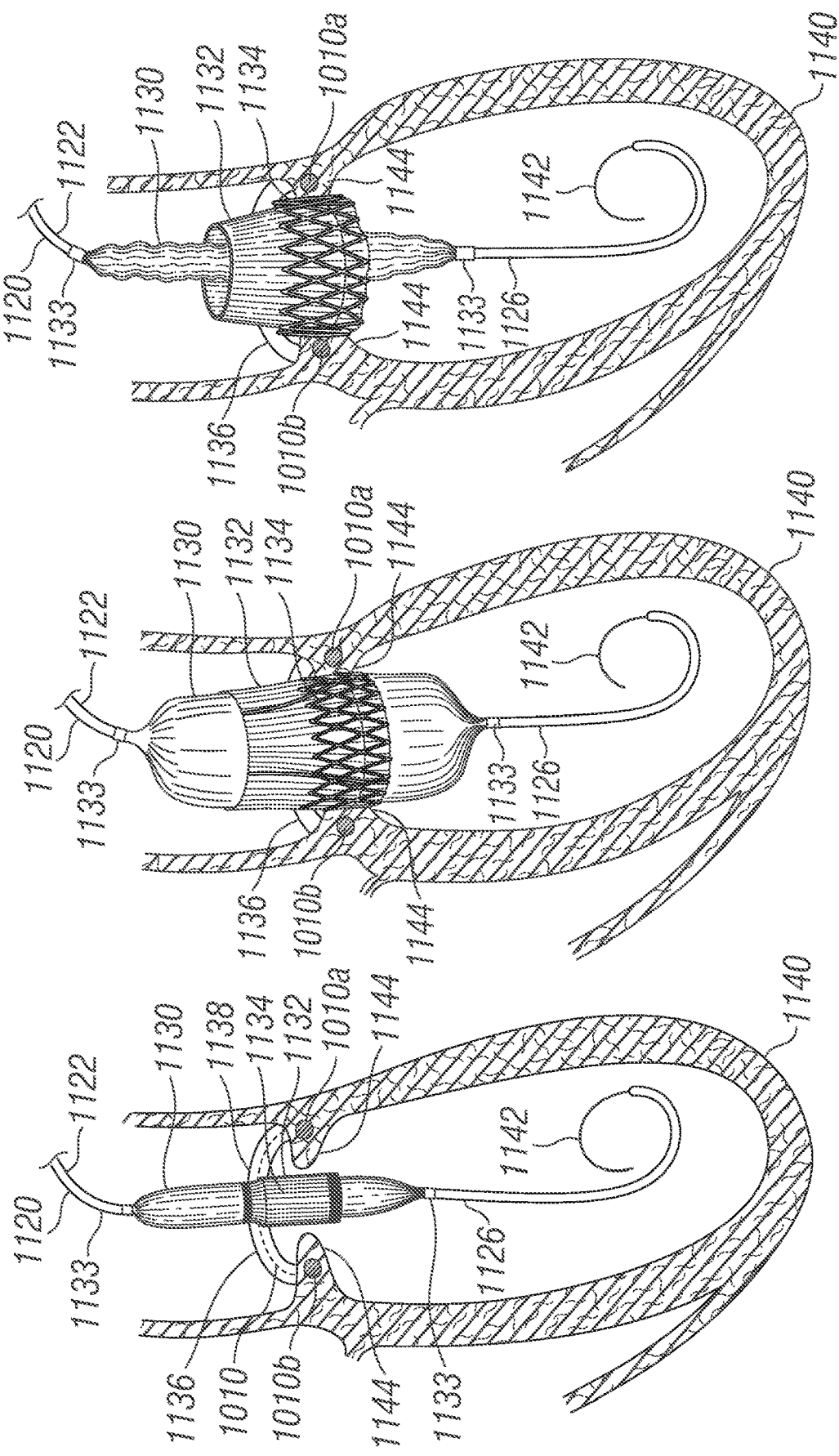

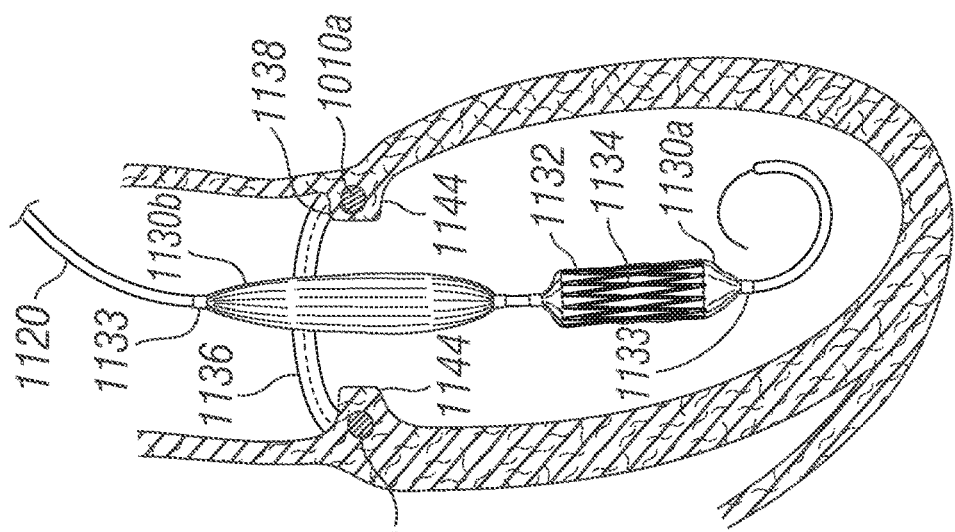
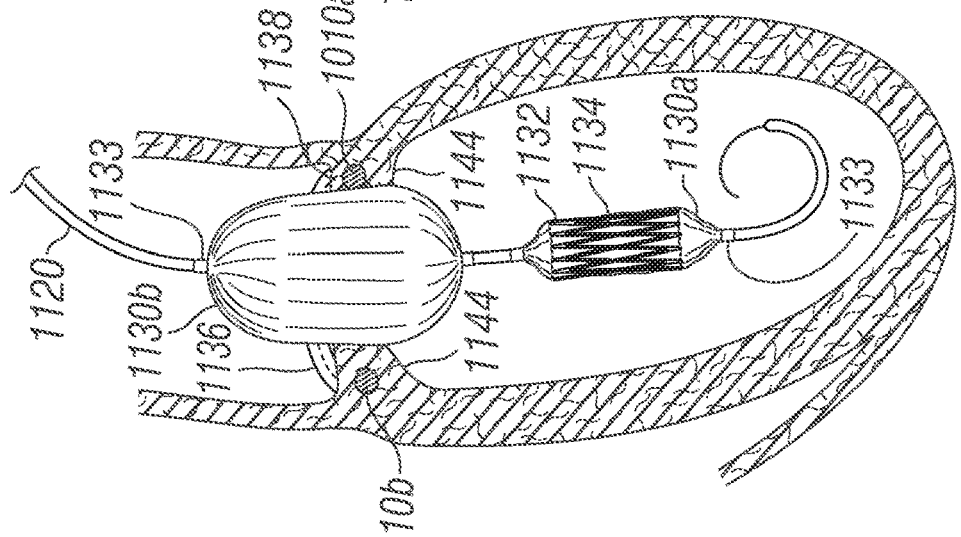
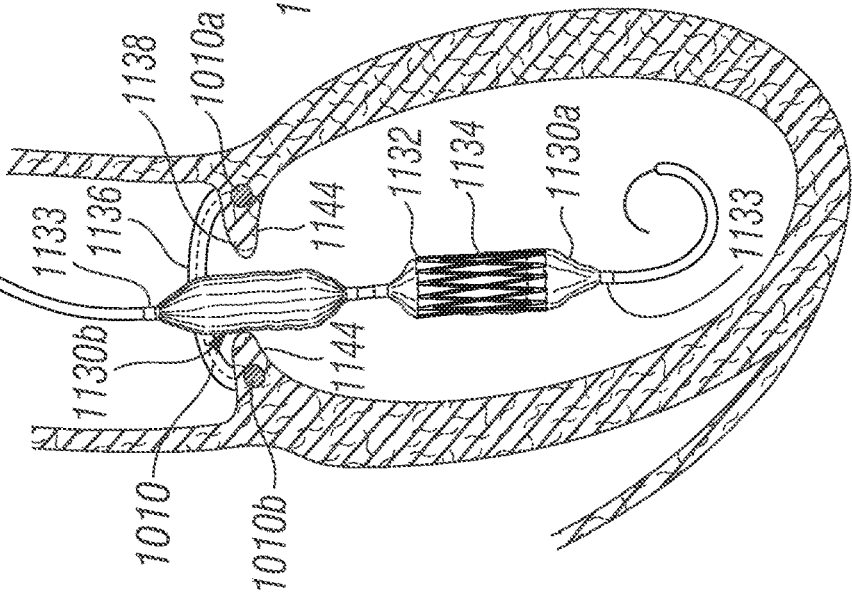

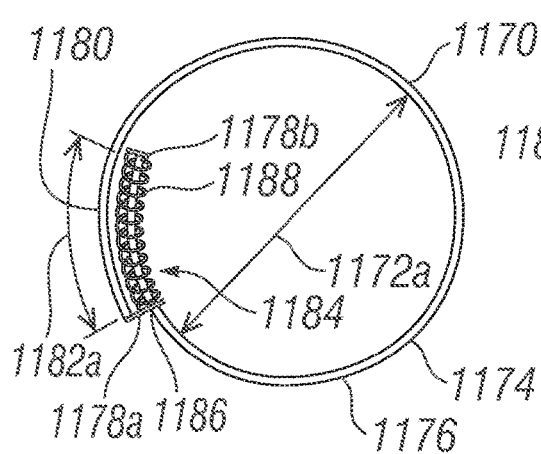 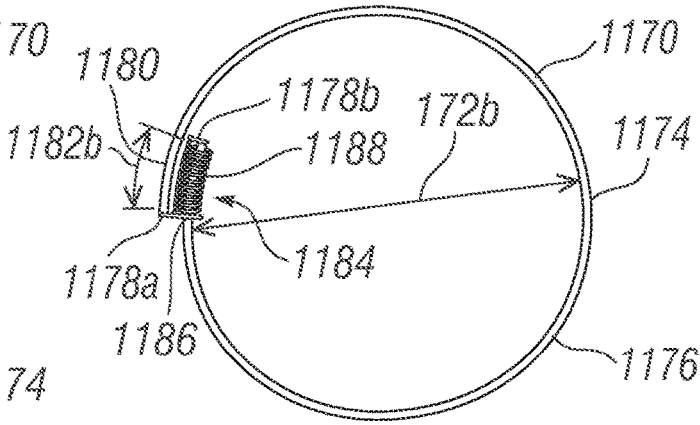

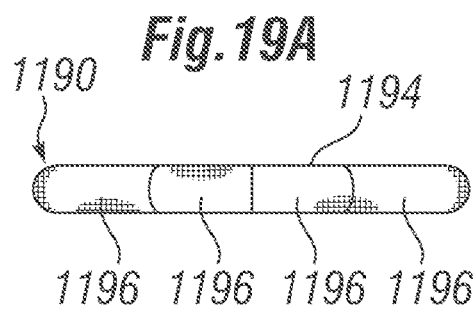
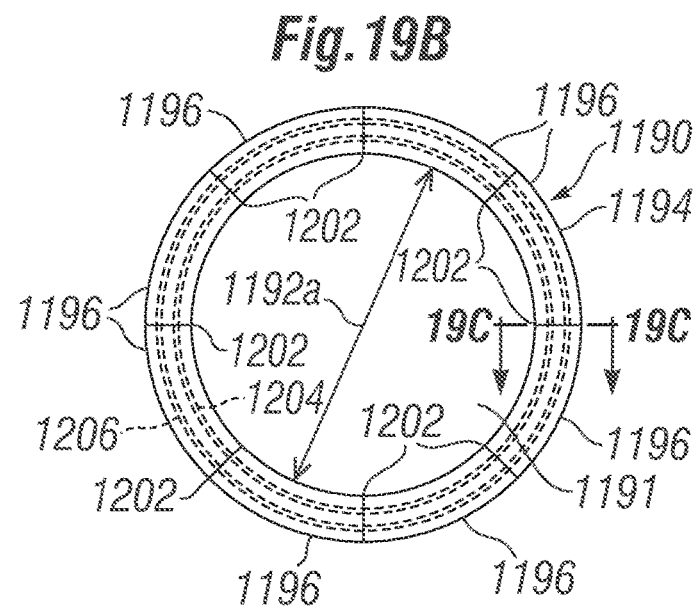
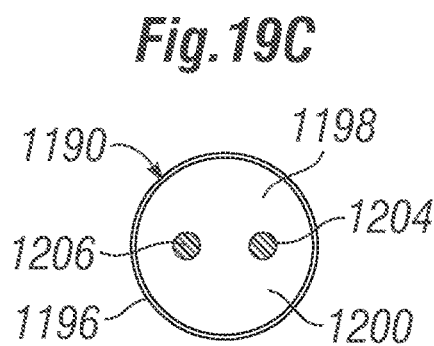
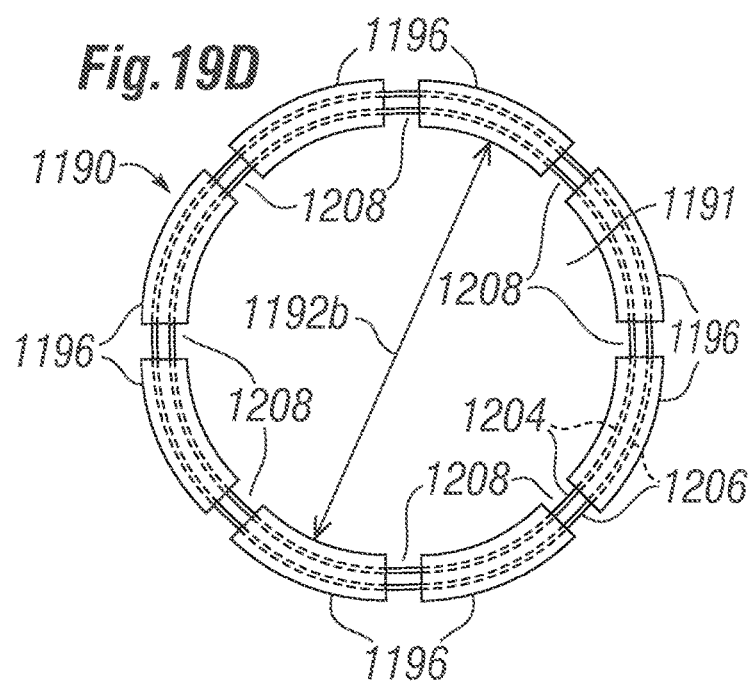

METHOD FOR CONVERTING AN ANNULOPLASTY RING IN VIVO

CROSS REFERENCE TO RELATED PATENT APPLICATIONS

This application is a divisional of U.S. application Ser. No. 15/498,213, filed Apr. 26, 2017, which is a continuation of U.S. application Ser. No. 14/038,357, filed Sep. 26, 2013, now U.S. Pat. No. 9,636,219, which is a continuation of U.S. application Ser. No. 12/234,559, filed Sep. 19, 2008, now U.S. Pat. No. 9,314,335, the entire disclosures all of which are incorporated herein by reference for all purposes. The present application is also related to U.S. patent application Ser. No. 12/234,580, filed Sep. 19, 2008, now U.S. Pat. No. 8,287,591, the entire disclosure which is incorporated herein by reference for all purposes.

FIELD OF THE INVENTION

The present invention relates to prosthetic cardiac implants for heart valve replacement and/or repair, and more particularly to a prosthetic heart valve and a prosthetic annuloplasty ring configured to receive an expandable prosthetic heart valve therein.

BACKGROUND OF THE INVENTION

In humans and other vertebrate animals, the heart is a hollow muscular organ having four pumping chambers separated by four heart valves: aortic, mitral (or bicuspid), tricuspid, and pulmonary. The valves open and close in response to a pressure gradient during each cardiac cycle of relaxation and contraction to control the flow of blood to a particular region of the heart and/or to blood vessels (pulmonary, aorta, etc.)

These valves are comprised of a dense fibrous ring known as the annulus, and leaflets or cusps attached to the annulus. For some valves, there is also a complex of chordae tendineae and papillary muscles securing the leaflets. The size of the leaflets or cusps is such that when the heart contracts the resulting increased blood pressure formed within heart chamber forces the leaflets open to allow flow from the heart chamber. As the pressure in the heart chamber subsides, the pressure in the subsequent chamber or blood vessel becomes dominant, and presses back against the leaflets. As a result, the leaflets or cusps come in apposition to each other, thereby closing the passage.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Various surgical techniques may be used to replace or repair a diseased or damaged valve. In a traditional valve replacement operation, the damaged leaflets are typically excised and the annulus sculpted to receive a replacement prosthetic valve. In a traditional valve repair, surgeons insert a ring around the valve to bring the valves into contact with each other, a procedure known as "annuloplasty."

In many patients who suffer from dysfunction of the mitral and/or tricuspid valves(s) of the heart, surgical repair of the valve (i.e., "valvuloplasty") is a desirable alternative to valve replacement. Remodeling of the valve annulus (i.e., "annuloplasty") is central to many reconstructive valvuloplasty procedures. In 1968, Dr. Alain Carpentier published studies which demonstrated that such remodeling of the valve annulus might be accomplished by implantation of a prosthetic ring (i.e. "annuloplasty ring") to stabilize the annulus and to correct or prevent valvular insufficiency that may result from defect dysfunction of the valve annulus. The annuloplasty ring is designed to support the functional changes that occur during the cardiac cycle: maintaining coaptation and valve integrity to prevent reverse flow while permitting good hemodynamics during forward flow. Annuloplasty procedures are performed not only to repair damaged or diseased annuli, but also in conjunction with other procedures, such as leaflet repair.

The annuloplasty ring typically comprises an inner substrate of a metal such as stainless or titanium, or a flexible material such as silicone rubber or Dacron cordage, covered with a biocompatible fabric or cloth to allow the ring to be sutured to the heart tissue. Annuloplasty rings may be stiff or flexible, may be split or continuous, and may have a variety of shapes, including circular, D-shaped (including kidney-shaped), or C-shaped. Examples are seen in U.S. Pat. Nos. 4,042,979; 4,290,151; 4,489,446; 4,602,911; 5,041,130; 5,061,277; 5,104,407; 5,201,880; 5,258,021; 5,607,471; and 6,187,040, the contents of each of which is hereby incorporated by reference in its entirety.

For some patients, however, the condition of the native heart valve requires complete replacement using a prosthetic heart valve. Prosthetic heart valves have been known for some time, and have been successfully implanted using traditional open-chest surgical approaches, minimally-invasive procedures, and so-called percutaneous methods.

A prosthetic heart valve typically comprises a support structure (such as a ring and/or stent) with a valve assembly deployed therein. The support structure is often rigid, and can be formed of various biocompatible materials, including metals, plastics, ceramics, etc. Two primary types of "conventional" heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the entire disclosures of which are hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. Components of the valve are usually assembled with one or more biocompatible fabric (e.g., Dacron) coverings, and a fabric-covered sewing ring is provided on the inflow end of the peripheral support structure.

In many bioprosthetic-type valves, a metallic or polymeric structure provides base support for the flexible leaflets, which extend therefrom. One such support is a "support frame," sometimes called a "wireform" or "stent," which has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus. One example of the construction of a flexible leaflet valve is seen in U.S. Pat. No. 6,585,766 to Huynh, et al. (issued Jul. 1, 2003), in which the exploded view of FIG. 1 illustrates a fabric-covered wireform 54 and a fabric-covered support stent 56 on either side of a leaflet subassembly 52. The contents of U.S. Pat. No. 6,585,766 are hereby incorporated by reference in their entirety. Other examples of valve and related assemblies/systems are found in U.S. Pat. No. 7,137,184, which issued on Nov. 21, 2006, the contents of which are hereby incorporated by reference in their entirety.

Sometimes the need for complete valve replacement may arise after a patient has already had an earlier valve replacement or repair using an annuloplasty ring for the same valve. For example, a native heart valve that was successfully repaired using an annuloplasty ring may suffer further damage years after the annuloplasty ring was implanted. Similarly, a prosthetic heart that was successfully implanted to replace a native valve may itself suffer damage and/or wear and tear many years after initially being implanted.

Implanting a prosthetic heart valve into a patient with a previously-implanted prosthetic heart valve or annuloplasty ring typically involves additional steps from a similar procedure in a patient with no previously-implanted heart valve or annuloplasty ring. Implanting the prosthetic heart valve directly within a previously-implanted prosthetic heart valve is generally impractical, in part because the new prosthetic heart valve (including the support structure and valve assembly) will have to reside within the annulus of the previously-implanted heart valve, and traditional prosthetic heart valves are not configured to easily receive such a valve-within-a-valve implantation in a manner which provides secure seating for the new valve while also having a large enough annulus within the new valve to support proper blood flow therethrough. Implanting the prosthetic heart valve directly within a previously-implanted annuloplasty ring is generally impractical, largely because most prosthetic heart valves have a generally circular shape whereas most annuloplasty rings are generally non-circular (including "D" and dog-bone shapes). Implanting a prosthetic heart valve in a patient who previously had a prosthetic heart valve or annuloplasty ring generally requires the previously-implanted heart valve or annuloplasty ring to be removed during the same procedure in which the new prosthetic heart valve is implanted. In such cases, a surgeon can use a traditional surgical approach to install the prosthetic valve, which can involve the surgeon cutting out the previously-implanted heart valve or annuloplasty ring from the heart valve annulus, and then implanting the new prosthetic valve into the heart valve annulus.

Percutaneous and minimally-invasive heart valve replacement has been developed recently, wherein a prosthetic heart valve is advanced percutaneously (e.g., via the femoral artery or other desired approaches) or via other approaches (i.e., minimally-invasive "keyhole" surgery, including approaches via the apex of the heart, etc.) into the heart valve annulus, and then expanded within the heart valve annulus. Various expandable valves are being tested, primarily that use balloon- or self-expanding stents as anchors. For the purpose of inclusivity, the entire field will be denoted herein as the delivery and implantation of expandable valves, regardless of whether the delivery method involves percutaneous, minimally-invasive, or other delivery methods. These valves typically include a scaffold or frame that expands radially outward into direct anchoring contact with the annulus, sometimes assisted with barbs. Examples of percutaneous heart valves and delivery systems and methods therefore are described in U.S. Pat. No. 5,411,552, issued May 2, 1995; U.S. Pat. No. 5,840,081, issued Nov. 24, 1998; U.S. Pat. No. 6,168,614, issued Jan. 2, 2001; and U.S. Pat. No. 6,582,462, issued Jun. 24, 2003; and also in U.S. patent application Ser. No. 11/280,062, filed Nov. 16, 2005; U.S. patent application Ser. No. 11/488,510, filed Jul. 18, 2006; and U.S. patent application Ser. No. 11/542,087, filed Oct. 2, 2006; the contents of each of which are hereby incorporated by reference in their entirety.

Percutaneous heart valve replacement is often performed without cutting out the native heart valve, wherein the prosthetic heart valve is expanded in the native heart valve annulus and the native valve leaflets are pressed against the valve annulus walls by the expanded prosthetic heart valve. However, in cases where a previously-implanted prosthetic heart valve or annuloplasty ring is present, deploying a prosthetic heart valve within the native heart valve annulus may be impractical. The shape and structure of the previously-installed prosthetic heart valve or annuloplasty ring may interfere with the proper placement, deployment, and functioning of the new prosthetic heart valve.

There is thus a need for a prosthetic heart valve which will properly replace a damaged heart valve, but will also enable a replacement expandable prosthetic heart valve to be deployed therein at a later time. There is also a need for an annuloplasty prosthesis and implantation device which will properly reshape/repair a damaged heart valve, but will also enable a prosthetic heart valve to be deployed therein at a later time. The current invention meets this need.

SUMMARY OF THE INVENTION

The invention is a prosthetic heart valve and an annuloplasty ring configured to receive a prosthetic heart valve, such as a catheter-deployed (transcatheter) prosthetic heart valve, therein. In one embodiment, the prosthetic heart valve has a support structure which is generally resistant to expansion when deployed in the patient's native heart valve annulus to replace the native heart valve (or to replace another prosthetic heart valve), but is configured to transform to a generally expanded and/or expandable configuration in order to receive a prosthetic heart valve therein. In another embodiment, the annuloplasty ring has a generally non-circular shape when deployed in the patient's native heart valve to correct heart valve function, but is configured to assume a generally circular configuration when subjected to a dilation force such as that provided by a dilation balloon used to deploy a prosthetic valve. The annuloplasty ring or prosthetic heart valve of the invention can be deployed using various surgical techniques (e.g., traditional open-chest, minimally-invasive, percutaneous, etc.) to correct heart valve function, and the expandable prosthetic valve can be deployed within the same native valve annulus at a much later time. The annuloplasty ring is configured to accept and even improve deployment of the prosthetic valve within the native valve annulus. The transformation from expansion-resistant to expanded/expandable, and/or from generally non-circular shape to generally circular configuration, can be achieved by subjecting the heart valve or annuloplasty ring support structure to an outward force, such as a dilation force, which may be provided by a dilation balloon used to deploy a replacement prosthetic valve.

The prosthetic heart valve structure may be generally rigid prior to dilation, and may be configured to become generally non-rigid, and even generally elastic, when subjected to an outward force. The elasticity may assist in holding a percutaneously-introduced prosthetic valve within the current prosthetic valve structure.

The prosthetic valve can be initially deployed in the patient's valve annulus using various surgical techniques (e.g., traditional open-chest, minimally-invasive, percutaneous, etc.) to correct heart valve function. If the heart valve function declines further after deployment of the prosthetic valve, a new replacement prosthetic valve can be deployed within the previously-deployed prosthetic valve without the need to excise the previously-deployed prosthetic valve. Deployment of the replacement prosthetic valve within the previously-deployed prosthetic valve can occur at a much later time from initial deployment of the previously-deployed prosthetic valve. The prosthetic valve of the current invention is configured to be deployed in a patient and, at a later time, to accept and even improve deployment of a replacement prosthetic valve within the same valve annulus.

In one embodiment, the structure can include a core comprising a spring, a plastically deformable material (including breakable materials), etc. The core may be formed as a single piece (possibly with one or more weakened sections configured to fail when subjected to a sufficient force), or may be formed from several segments connected at seams. The core may form an inner lumen through which further attachment devices may be passed, such as elastic and/or inelastic cords.

A prosthetic valve according to an embodiment of the invention may include a cover configured to hold the core together after it has been dilated. For example, where a core breaks into multiple pieces during dilation, the cover can serve to keep the pieces from separating from the prosthetic valve. The cover can also serve to hold the core and/or other portions of the support frame in a desired shape, and may have elastic properties.

In an embodiment of the invention, the prosthetic valve is a stented bioprosthetic valve configured to expand and contract dynamically within the patient's annulus. The dynamic motion of the annulus can enable the valve opening to expand during periods of peak demand, and reduce the annular restriction to the increased flow. The expansion can also decrease leaflet stresses associated with potential higher gradients. The expansion can also permit later placement of an expandable prosthetic valve within the stented bioprosthetic valve.

In an embodiment of the invention, a prosthetic valve has a support structure having a generally rigid and/or expansion-resistant portion including a core. The prosthetic valve may include plastically deformable materials configured to maintain the prosthetic valve support structure in the generally rigid and/or expansion-resistant shape for deployment. The plastically deformable materials may be configured to break or otherwise plastically deform and no longer maintain the support structure in the generally rigid and/or expansion-resistant configuration when subjected to a dilation force. The support structure may form a continuous loop, and may include elastically deformable material configured to provide tension about the continuous loop after the support structure has been dilated by a dilation balloon.

A method for repairing a patient's heart function according to an embodiment of the invention can include: providing a prosthetic heart valve configured to have a generally rigid and/or expansion-resistant support structure upon implantation and also configured to assume a generally non-rigid and/or expanded/expandable configuration upon dilation; and implanting the prosthetic heart valve in a heart valve annulus. The method may also include deploying an expandable prosthetic heart valve within the previously-deployed heart valve and heart valve annulus. Deploying the expandable prosthetic heart valve within the previously-deployed prosthetic valve and heart valve annulus may include dilating the previously-deployed prosthetic valve to cause the previously-deployed prosthetic valve to assume a generally non-rigid and/or expanded/expandable shape.

Dilating a previously-deployed prosthetic heart valve may include using a dilation balloon, such as the type currently used for dilation of native heart valves, which can be advanced within the previously-deployed prosthetic heart valve and expanded to a desired pressure and/or diameter. As a general rule, dilation balloons used for dilation of native valves are formed from generally inelastic material to provide a generally fixed (i.e., pre-set) outer diameter when inflated. Once such balloons are inflated to their full fixed diameter, they will not appreciably expand further (prior to rupturing) even if additional volume/pressure is added therein. Typical pressures for inflating such balloons are between 1 and 6 atmospheres, with pre-set inflated outer diameters of such balloons being on the order of 18 to 33 millimeters. The dilation balloon may be expanded to a desired pressure (e.g., 1-6 atmospheres) sufficient to fully inflate the dilation balloon to its desired diameter and to dilate and expand the previously-deployed prosthetic heart valve.

A typical surgically-implanted prosthetic heart valve will withstand dilation pressures of several atmospheres such as provided by most dilation balloons without expanding and/or becoming elastic. By contrast, the prosthetic heart valve of the current invention is configured to become expanded and/or generally elastic when subjected to sufficient pressure provided by a dilation balloon. If the dilation balloon is expanded, using sufficient pressure, to an expanded outer diameter larger than the inner diameter of the prosthetic heart valve of the invention, the prosthetic heart valve will expand in diameter and/or become elastic.

In one embodiment, the dilation balloon is configured with a pre-set inflated outer diameter which is larger, such as by 10-20% or more, than the inner diameter of the previously-deployed prosthetic heart valve. As an example, if the previously-deployed prosthetic heart valve of the invention has an inner diameter of 23 mm, a dilation balloon having an inflated diameter of 24-27 mm may be inflated within the prosthetic heart valve to cause it to expand and/or become elastic.

Prosthetic heart valves according to various embodiments of the invention can be configured to be generally rigid prior to dilation, but become expanded and/or elastic when subjected to a sufficient dilation pressure. For example, a prosthetic heart valve could be configured to withstand naturally occurring dilation pressures that may occur during beating of the heart, but to become expanded and/or elastic when subjected to a desired pressure (e.g., from a dilation balloon), such as a pressure of 1 atmosphere, 2 atmospheres, 3 atmospheres, 4 atmospheres, 5 atmospheres, or 6 atmospheres, depending on the particular application.

Note that the dilation balloon inflated diameters and inflated pressures, as well as the pressures at which the prosthetic heart valve of the invention would become expanded and/or elastic, set forth above are by way of example, and that the use of balloons with other pressures and diameters, and of prosthetic heart valves configured to change shape and/or expand and/or become elastic when subjected to other pressures and expanded balloon diameters, are also within the scope of the invention.

An annuloplasty ring is being developed having a structure that can expand and/or otherwise change configuration in order to accept a percutaneously-delivered prosthetic heart valve therein. Such an annuloplasty ring is disclosed in U.S. patent application Ser. No. 12/234,580, filed Sep. 19, 2008 and entitled "Annuloplasty Ring Configured to Receive a Percutaneous Prosthetic Heart Valve Implantation," the entire contents of which are incorporated herein by reference. In an embodiment of the invention, the annuloplasty ring defines a first inner orifice area when deployed in the patient's native heart valve to correct heart valve function, but is configured to define a second inner orifice area when subjected to a dilation force such as that provided by a dilation balloon used to deploy a prosthetic valve, with the second (dilated) orifice area being larger than the first (pre-dilation) orifice area. In an annuloplasty ring which is generally circular both before and after dilation, the first inner orifice area has a corresponding first inner diameter, and the second inner orifice area has a corresponding second inner diameter, with the second (post-dilation) inner diameter being larger than the first (pre-dilation) inner diameter.

In one embodiment, the annuloplasty ring has a generally curved portion and a generally straight portion, with the generally curved portion being generally rigid and the generally straight portion being generally flexible. The annuloplasty ring may form a continuous loop or a discontinuous loop, and/or may be generally "D"-shaped (including kidney shapes) or otherwise generally non-circular. The ring may include upward and/or downward structures, such as bows, when viewed from the side.

In an embodiment of the invention, an annuloplasty ring is a discontinuous structure having a generally rigid curved portion and two generally straight portions extending therefrom, with the generally straight portions aligned with each other to form a generally straight (but discontinuous) structure.

An embodiment of the invention includes a first generally rigid section, a second generally rigid section, and a restraint configured to prevent movement of the first generally rigid section with respect to the second generally rigid section, with the restraint further configured to permit movement of the first generally rigid section with respect to the second generally rigid section when the annuloplasty ring is subjected to a dilation force. The restraint may be configured to permit rotational movement of the first generally rigid section with respect to the second generally rigid section when the annuloplasty ring is subjected to the dilation force. The restraint may comprise a lock configured to fail when the annuloplasty ring is subjected to a dilation force. The restraint may comprise suture, an elastic material or structure such as a spring, a plastically deformable material (including breakable materials), etc.

An annuloplasty ring according to an embodiment of the invention may include a movable connection between the first generally rigid section and the second generally rigid section, wherein the movable connection is configured to survive application of the dilatation force. The movable connection may comprise a hinge, a generally flexible material such as tether, etc.

In an embodiment of the invention, an annuloplasty ring has a generally non-circular shape and has a generally rigid portion defining at least half of the circumference of the generally non-circular shape, and the annuloplasty ring is configured to assume a generally circular shape when dilated by a balloon catheter. The annuloplasty ring may include plastically deformable materials configured to maintain the annuloplasty ring in the generally non-circular shape. The plastically deformable materials may be configured to break or otherwise plastically deform and no longer maintain the annuloplasty ring in the generally non-circular shape when subjected to a dilation force. The annuloplasty ring may form a continuous loop, and may include elastically deformable material configured to provide tension within the continuous loop.

A method for repairing a patient's heart function according to an embodiment of the invention can include: providing an annuloplasty ring having a generally non-circular configuration but configured to assume a generally circular configuration when subjected to a dilatational force; and implanting the annuloplasty ring in a heart valve annulus. The method may also include deploying an expandable prosthetic heart valve within the annuloplasty ring and heart valve annulus. Deploying the expandable prosthetic heart valve within the annuloplasty ring and heart valve annulus may include dilating the annuloplasty ring to cause the annuloplasty ring to assume a generally circular shape.

The generally non-circular configuration of the ring may be a "D"- or kidney-shape, so-called dog-bone shape, etc.

Dilating an annuloplasty ring may include using a dilation balloon, such as the type currently used for dilation of native heart valves, which can be advanced within the annuloplasty ring and expanded to a desired pressure and/or diameter. As a general rule, dilation balloons used for dilation of native valves are formed from generally inelastic material to provide a generally fixed (i.e., pre-set) outer diameter when inflated. Once such balloons are inflated to their full fixed diameter, they will not appreciably expand further (prior to rupturing) even if additional volume/pressure is added therein. Typical pressures for inflating such balloons are between 1 and 6 atmospheres, with pre-set inflated outer diameters of such balloons being on the order of 18 to 33 millimeters. The dilation balloon may be expanded to a desired pressure (e.g., 1-6 atmospheres) sufficient to fully inflate the dilation balloon to its desired diameter and to dilate and expand the native valve and annuloplasty ring.

A typical rigid annuloplasty ring will withstand dilation pressures of several atmospheres such as provided by most dilation balloons without expanding and/or becoming elastic. By contrast, the annuloplasty ring of the current invention is configured to change shape and/or become expanded and/or generally elastic when subjected to sufficient pressure provided by a dilation balloon. If the dilation balloon is expanded, using sufficient pressure, to an expanded outer diameter larger than the inner diameter of the native valve and annuloplasty ring, the annuloplasty ring will expand in diameter and/or change shape and/or become elastic.

In one embodiment, the dilation balloon is configured with a pre-set inflated outer diameter which is larger, such as by 10-20% or more, than the inner diameter of the annuloplasty ring. As an example, if the annuloplasty ring of the invention has an inner diameter of 23 mm, a dilation balloon having an inflated diameter of 24-27 mm may be inflated within the annuloplasty ring to cause it to expand and/or become elastic.

Annuloplasty rings according to various embodiments of the invention can be configured to be generally rigid prior to dilation, but change shape and/or become expanded and/or elastic when subjected to a sufficient dilation pressure. For example, an annuloplasty ring could be configured to withstand naturally occurring dilation pressures that may occur during beating of the heart, but to become expanded and/or elastic when subjected to a desired pressure (e.g., from a dilation balloon), such as a pressure of 1 atmosphere, 2 atmospheres, 3 atmospheres, 4 atmospheres, 5 atmospheres, or 6 atmospheres, depending on the particular application.

Note that the dilation balloon inflated diameters and inflated pressures, as well as the pressures at which the annuloplasty ring of the invention would become expanded and/or elastic, set forth above are by way of example, and that the use of balloons with other pressures and diameters, and of annuloplasty rings configured to change shape and/or expand and/or become elastic when subjected to other pressures and expanded balloon diameters, are also within the scope of the invention.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 6A-6C depict top, side, and close-up sectional views, respectively, of a prosthetic heart valve support structure according to an embodiment of the invention;

FIG. 6D depicts a top view of the prosthetic heart valve support structure of FIGS. 6A-6C after the prosthetic heart valve support structure has been dilated;

FIG. 8A depicts an expandable prosthetic heart valve deployment catheter configured for annuloplasty ring dilation and expandable prosthetic heart valve deployment according to an embodiment of the invention;

FIG. 9A depicts an expandable prosthetic heart valve deployment catheter configured for dilation of a previously-deployed prosthetic heart valve and for deployment of an expandable prosthetic heart valve according to an embodiment of the invention;

FIG. 9B depicts the expandable prosthetic heart valve deployment catheter of FIG. 9A with the dilation balloon positioned within the previously-deployed prosthetic heart valve in the heart valve annulus according to an embodiment of the invention;

FIG. 9C depicts the expandable prosthetic heart valve deployment catheter of FIG. 9A dilating the previously-deployed prosthetic heart valve according to an embodiment of the invention;

FIG. 9D depicts the expandable prosthetic heart valve deployment catheter of FIG. 9A with the dilation balloon deflated after dilation of the previously-deployed prosthetic heart valve according to an embodiment of the invention;

FIG. 10 depicts an annuloplasty ring deployed in a heart according to an embodiment of the invention;

FIG. 15A depicts a prosthetic heart valve deployment catheter configured for annuloplasty ring dilation and prosthetic heart valve deployment according to an embodiment of the invention;

FIG. 15B depicts the prosthetic heart valve deployment catheter of FIG. 15A positioned within a heart valve annulus of a patient according to an embodiment of the invention;

FIG. 15C depicts the prosthetic heart valve deployment catheter of FIG. 15A dilating the annuloplasty ring and deploying the prosthetic heart valve according to an embodiment of the invention;

FIG. 15D depicts the prosthetic heart valve deployment catheter of FIG. 15A being withdrawn from the patient according to an embodiment of the invention;

FIG. 16A depicts a prosthetic heart valve deployment catheter configured for annuloplasty ring dilation and prosthetic heart valve deployment according to an embodiment of the invention;

FIG. 16B depicts the prosthetic heart valve deployment catheter of FIG. 16A with the proximal dilation balloon positioned within the heart valve annulus according to an embodiment of the invention;

FIG. 16C depicts the prosthetic heart valve deployment catheter of FIG. 16A dilating the annuloplasty ring according to an embodiment of the invention;

FIG. 16D depicts the prosthetic heart valve deployment catheter of FIG. 16A with the proximal dilation balloon deflated according to an embodiment of the invention;

FIGS. 18A and 18B depict top views, in pre-dilation and post-dilation configurations, of an annuloplasty ring according to an embodiment of the invention;

FIGS. 19A-19C depict top, side, and cross-sectional views, respectively, of an annuloplasty ring according to an embodiment of the invention;

FIG. 19D depicts a top view, in expanded configuration, of the annuloplasty ring of FIGS. 19A-19C.

DETAILED DESCRIPTION OF PREFERRED EMBODIMENTS

Figure 1:
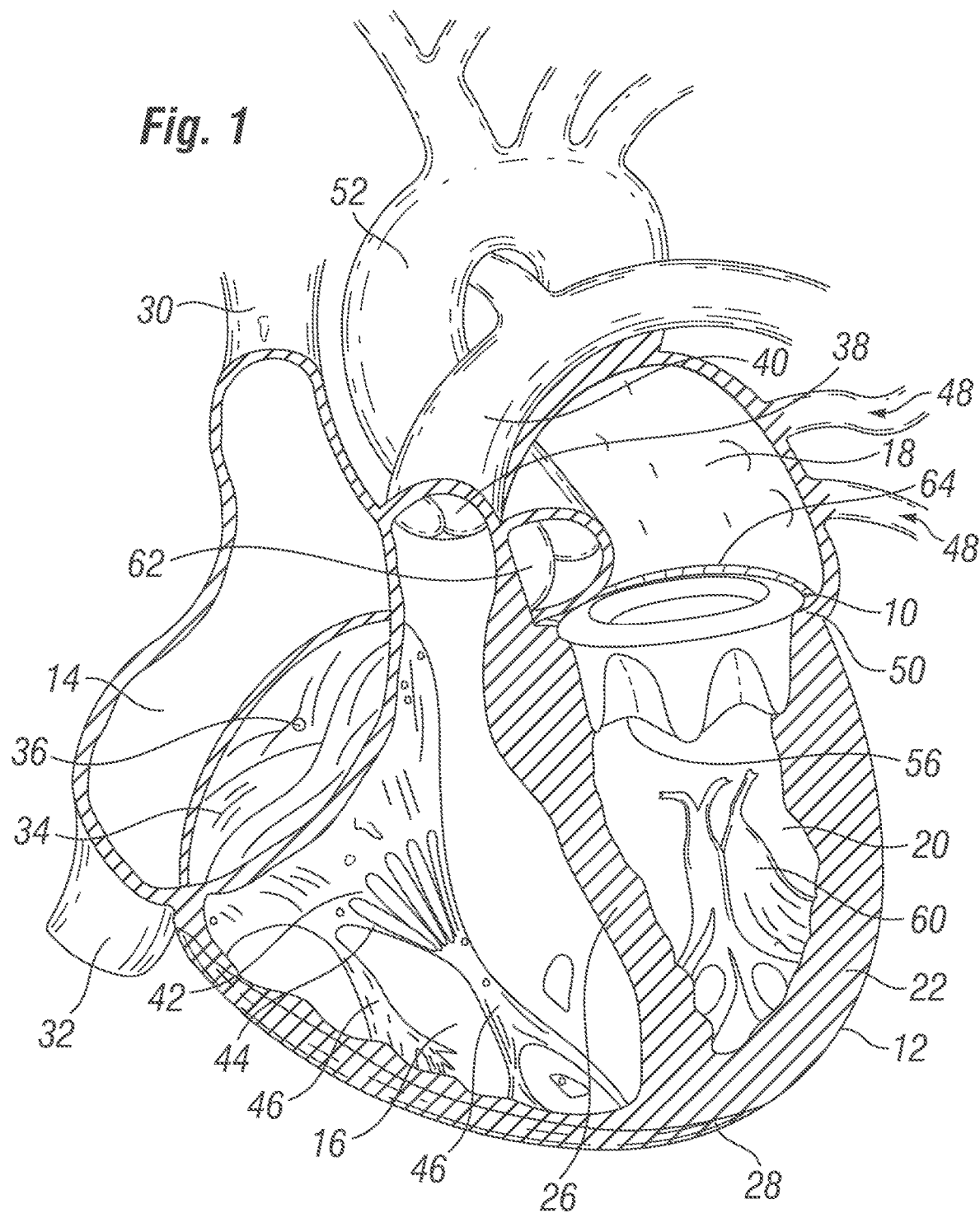
FIG. 1 depicts a prosthetic heart valve deployed in a heart according to an embodiment of the invention.

With reference to FIG. 1, a prosthetic heart valve 10 according to the invention is depicted in a heart 12. The heart 12 has four chambers, known as the right atrium 14, right ventricle 16, left atrium 18, and left ventricle 20. The general anatomy of the heart 12, which is depicted as viewed from the front of a patient, will be described for background purposes. The heart 12 has a muscular outer wall 22, with an interatrial septum 24 dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendineae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve in a normal heart controls blood flow between the left atrium 18 and the left ventricle 20. Note that in the current figure, the native mitral valve has been replaced with the prosthetic heart valve 10, which is accordingly a prosthetic mitral valve 50. The prosthetic mitral valve 50 is closed during ventricular systole when blood is ejected from the left ventricle 20 into the aorta 52. Thereafter, the prosthetic mitral valve 50 is opened to refill the left ventricle 20 with blood from the left atrium 18. Blood from the left ventricle 20 is pumped by power created from the musculature of the heart wall 22 and the muscular interventricular septum 26 through the aortic valve 62 into the aorta 52 which branches into arteries leading to all parts of the body.

In the particular embodiment depicted, the prosthetic heart valve 10 is deployed to replace a native mitral valve, and more particularly is secured (via, e.g., sutures) adjacent and around the mitral valve annulus 64. Depending on the particular application, including the method by which the prosthetic heart valve 10 was implanted, the particular native valve (mitral, tricuspid, etc.) and/or some or all of its associated structures may be entirely or partially removed prior to or during implantation of the prosthetic heart valve 10, or the native valve and/or some or all associated structures may simply be left in place with the prosthetic heart valve 10 installed over the native valve. For example, a native mitral valve typically has two leaflets (anterior leaflet and posterior leaflet), lower portions and free edges of which are connected via mitral chordae tendineae to papillary muscles 60 in the left ventricle 20 for controlling the movements of the mitral valve. Not all of these structures (i.e., mitral valve leaflets, chordae tendineae) are depicted in FIG. 1 because, in the particular embodiment, the native mitral valve and many associated structures (chordae, etc.) have been removed prior to or during implantation of the prosthetic heart valve 10. However, in many prosthetic valve implantations, surgeons choose to preserve many of the chordae tendineae, etc., even when excising the native valve.

Although FIG. 1 depicts a prosthetic mitral valve, note that the invention can be applied to prosthetic valves (and systems and methods therefore) configured to replacement of any heart valves, including aortic, mitral, tricuspid, and pulmonary valves.

Figure 2A:
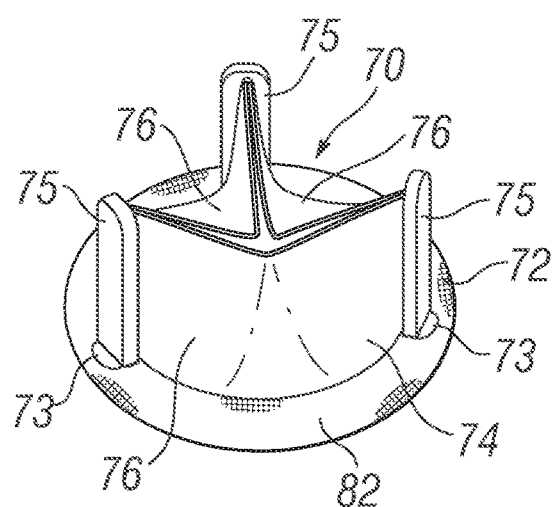
FIGS. 2A-2C depict perspective, top, and side views, respectively, of a prosthetic heart valve according to an embodiment of the invention.
Figure 2B:
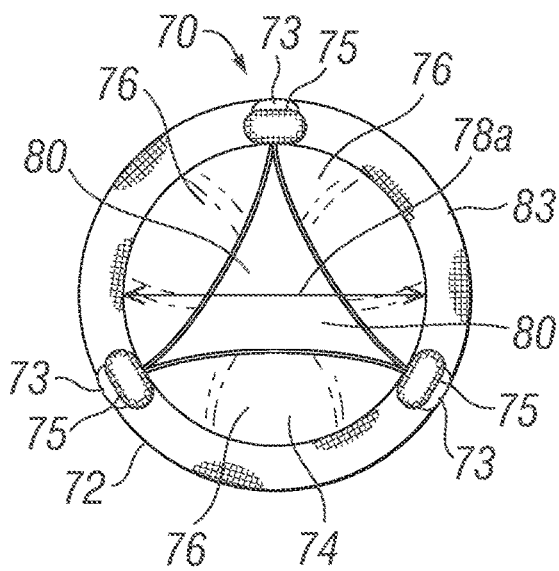
Figure 2C:
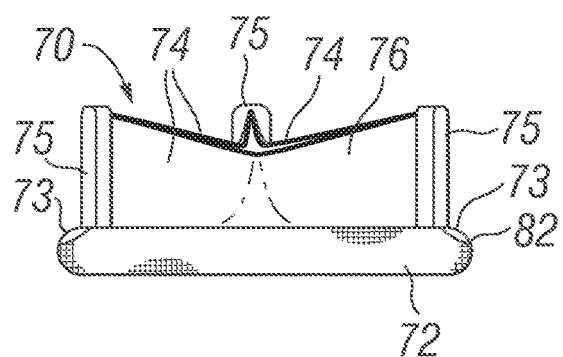

FIGS. 2A-2C depict a prosthetic heart valve 70 according to an embodiment of the invention, where the prosthetic heart valve 70 comprises a support frame 72 and valve structure 74. In the particular embodiment depicted, the valve structure 74 comprises three heart valve leaflets 76. The prosthetic heart valve 70 has an inner diameter 78a of a valve orifice 80 through which blood may flow in one direction, but the valve leaflets 76 will prevent blood flow in the opposite direction. The support frame 74 is generally rigid and/or expansion-resistant in order to maintain the particular shape (which in this embodiment is generally round) and diameter 78a of the valve orifice 80 and also to maintain the respective valve leaflets 76 in proper alignment in order for the valve structure 74 to properly close and open. The particular support frame 74 also includes commissure supports 75. In the particular embodiment depicted in FIGS. 2A-2C, the support frame 74 defines a generally rigid and/or expansion-resistant ring 82 which encircles the valve 70 and defines a generally round valve orifice 80, but other shapes are also within the scope of the invention, depending on the particular application (including issues such as the particular native valve to be replaced, etc.) The particular prosthetic heart valve 70 includes visualization markers 73 (such as radiopaque markers, etc.), which in the current embodiment are on the support frame 74 and correspond to the ring 82 and also to the commissure supports 75 (and hence to the commissures), which can aid in proper placement of a subsequently-deployed expandable prosthetic heart valve within the valve orifice 80 of the prosthetic heart valve 70.

Figure 2D:
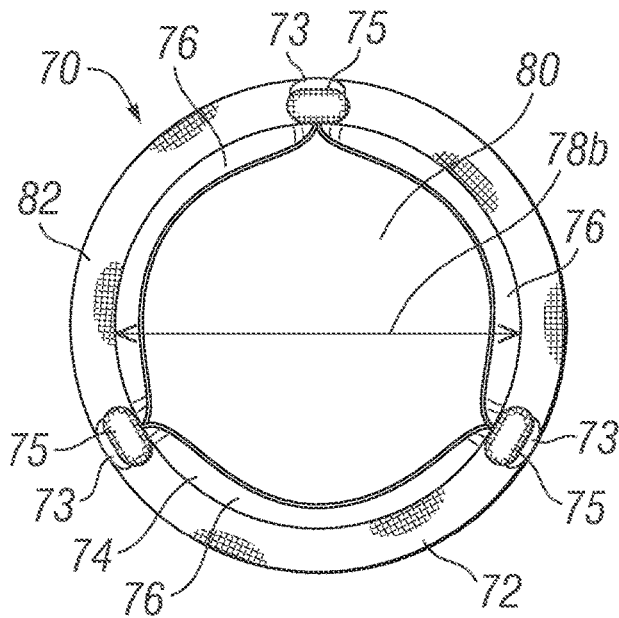
FIG. 2D depicts a top view of the prosthetic heart valve of FIGS. 2A-2C after the prosthetic heart valve has been dilated.

When the prosthetic heart valve 70 of FIGS. 2A-2C is subjected to a dilation force (such as that from a dilation balloon, which may provide pressures of 1 to 5 atmospheres), the prosthetic heart valve will be expanded somewhat. The support frame 74 will transition from the generally rigid and/or expansion-resistant configuration of FIGS. 2A-2C to a generally non-rigid and expanded configuration depicted in FIG. 2D. Note that the ring 82, which was generally rigid and/or expansion-resistant, is now generally non-rigid and is expanded, and the valve orifice 80 has accordingly been enlarged to a larger inner diameter 78b. The larger inner diameter 78b is configured to receive an expandable prosthetic heart valve therein. The overall result is that the "post-dilation" prosthetic heart valve 70 of FIG. 2D has a generally larger inner diameter circular opening 78b. The actual inner diameters will depend on the particular application, including aspects of the particular patient's heart (e.g., native valve and/or annulus diameter, etc.). As an example, the pre-dilation inner diameter 78a for a mitral valve may be between 25-33 mm, or for an aortic valve 18-28 mm. The post-dilation inner diameter 78b will be larger, and more specifically large enough to accommodate the outer diameter of an expandable prosthetic valve therein.

In some procedures where an expandable prosthetic heart valve is used to replace/repair a previously-deployed prosthetic heart valve, it may be desirable for the expandable prosthetic heart valve to have a deployed (expanded) inner diameter (and corresponding expandable prosthetic heart valve orifice area) approximately equal to the pre-dilation inner diameter 78a (and corresponding pre-dilation prosthetic valve orifice area) of the previously-deployed prosthetic heart valve 70. Such consistency between inner diameters/orifice areas can be useful in maintaining proper blood flow, so that the expandable prosthetic heart valve will provide the same blood flow as was provided by the previously-deployed prosthetic heart valve. Note that the term "valve orifice area" refers to the area of the valve orifice when the valve portion is in the fully open configuration (e.g., with the valve leaflets in their fully open configuration so that the effective orifice area is at its maximum size).

For example, Edwards Lifesciences has Sapien™ expandable prosthetic heart valves having outer diameters of 23 and 26 mm, respectively, which have corresponding inner diameters of about 20 and 23 mm, respectively. Accordingly, the post-dilation inner diameter 78b of the (previously-deployed) prosthetic heart valve may be on the order of 23 and 26 mm (respectively) to accommodate such expandable prosthetic heart valves. This corresponds to a post-dilation inner diameter 78b being about 10 to 20% larger than the pre-dilation inner diameter 78a. Accordingly, embodiments of the invention include a prosthetic heart valve having a post-dilation inner diameter 78b that is about 10, 15, or 20%, or between 5-25%, 10-20%, or 13-17% of the pre-dilation inner diameter 78a.

Note that the invention is not limited to the above differences between pre- and post-dilation inner diameters. For example, there may be applications where much smaller and/or much larger post-dilation inner diameters may be required. In some cases an expandable prosthetic heart valve will have an outer diameter only slightly larger than its inner diameter, so that less expansion of the previously-deployed prosthetic heart valve inner diameter is required in order to accommodate the expandable prosthetic heart valve. In other cases an expandable prosthetic heart valve may have an outer diameter that is much larger than its inner diameter, so that a greater expansion of the previously-deployed prosthetic heart valve inner diameter is necessary to accommodate the expandable prosthetic heart valve. There may also be applications where it may be desirable to deploy an expandable prosthetic heart valve having a smaller or larger inner diameter than was provided by the (previously-deployed and pre-dilation) prosthetic heart valve.

Note that, depending on the particular embodiment, a prosthetic heart valve 70 according to the invention may return to its pre-dilation inner diameter 78a after being subject to dilation such as from a balloon dilation catheter. However, the balloon dilation will have rendered the "post-dilation" prosthetic heart valve 70 into a generally non-rigid and/or expansion-friendly configuration, so that the "post-dilation" prosthetic heart valve 70 will be forced with relative ease into a larger diameter (such as 78b) when an expandable (e.g., balloon-expandable, self-expanding, etc.) prosthetic heart valve is deployed within the valve orifice 80 of the prosthetic heart valve 70.

Figure 3A:
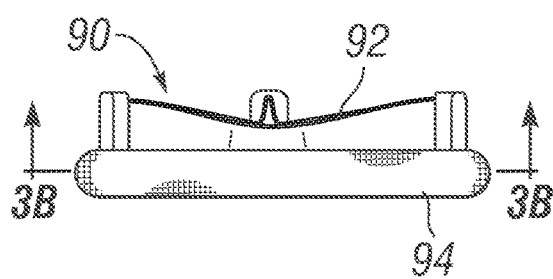
FIGS. 3A-3C depict side, top (in cross section), and close-up sectional views, respectively, of a prosthetic heart valve support structure according to an embodiment of the invention.
Figure 3B:
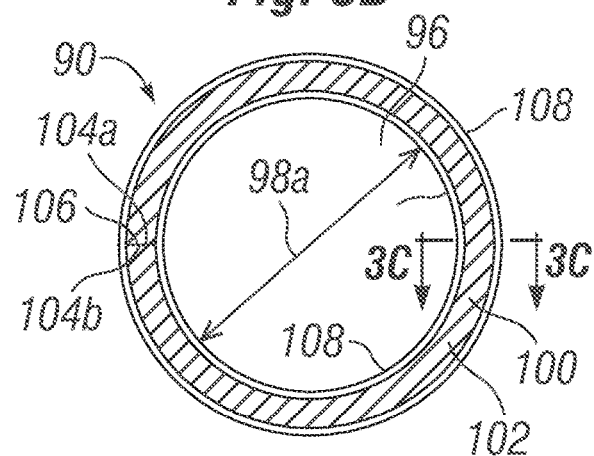
Figure 3C:
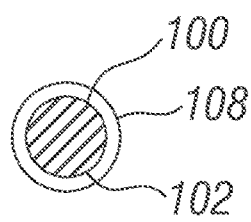

FIGS. 3A-3C depicts a prosthetic heart valve 90 having a valve structure 92 and support frame 94 according to a further embodiment of the invention, with the prosthetic heart valve 90 having a valve orifice 96 having an inner diameter 98a. The support frame 94 has a generally rigid and expansion-resistant core 100 formed from a single core element 102 which is bent or otherwise formed into a generally circular shape with opposing ends 104a, 104b meeting at a seam 106 so as to form the complete circle. The seam 106 may include adhesive, solder, welds, etc. in order to secure the two ends 104a, 104b together. The prosthetic heart valve 90 includes a covering 108 around the support core 96. The covering 108 may be a cloth-like material, and may be a sewing ring configured to be sewn to the native heart valve annulus during deployment of the prosthetic heart valve 90. The covering 108 is generally flexible, and may be generally elastic. The covering 108 (or a portion thereof) may also be generally compressible, especially in the portion facing inward toward the valve orifice 96, which can assist in seating an expandable valve therein. A compressible material may be applied onto or within the covering 108 in a position to provide a compressible region on the surface facing inward toward the valve orifice 96.

Figure 3D:
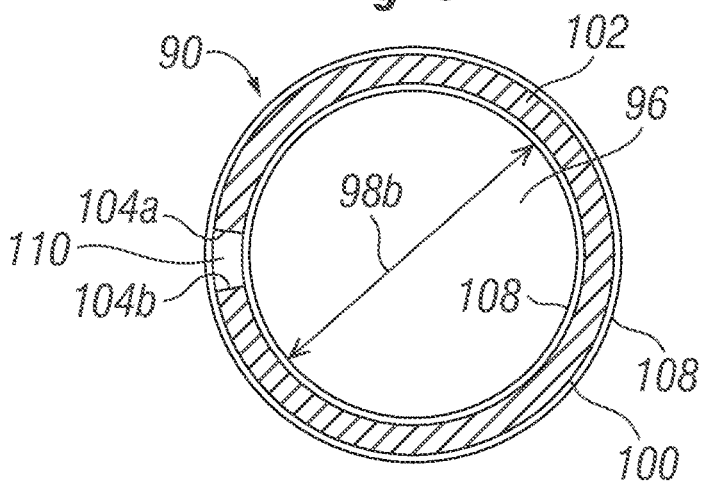
FIG. 3D depicts a top view of the prosthetic heart valve support structure of FIGS. 3A-3C after the prosthetic heart valve support structure has been dilated.

When the prosthetic heart valve 90 is subject to a dilation force such as that from a dilation balloon catheter, the support frame 94 will become non-rigid and expanded. More particularly, the seam 106 of the core 100 will rupture, so that the opposing ends 104a, 104b will be separated by an opening 110, and the core 100 will assume a generally C-shaped configuration as depicted in FIG. 3D. The covering 108 will stretch or otherwise expand circumferentially to accommodate the enlarged/expanded core 100, and the prosthetic heart valve 90 will have an enlarged inner diameter 98b for the valve orifice 96. Depending on the particular embodiment, including the particular construction of the core 100 and/or covering, the (post-dilation) prosthetic heart valve 90 may provide an inward (i.e., compressive) force toward the valve orifice 96. For example, the core 100 may be formed of a generally resilient spring-like material and/or memory material, and may be biased somewhat toward its non-dilated configuration (i.e., with the opposing ends 104a, 104b touching each other as in FIGS. 3A-3C). The covering 108 may also (or alternatively) be elastic and, after dilation of the prosthetic heart valve 90, may provide an inward pull on the core 100 so as to bias the opposing ends 104a, 104b toward each other. This inward pressure can help to seat an expandable heart valve that may be deployed within the prosthetic heart valve 90. In an embodiment where compressible material is provided (e.g., as part of the covering 108) facing inward toward the valve orifice 96, then the compressible material can provide additional assistance in seating an expandable heart valve within the prosthetic heart valve 90.

Figure 4A:
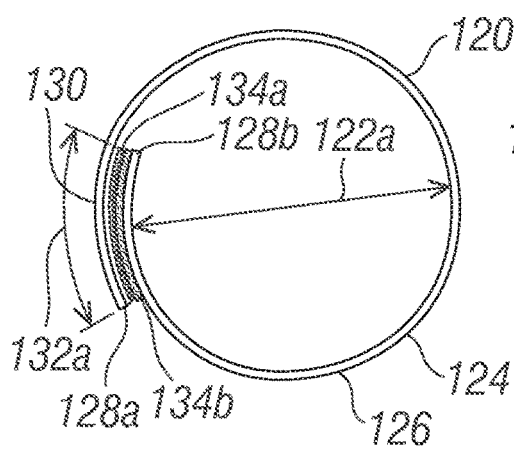
FIGS. 4A-4B depict top views of a prosthetic heart valve support structure in pre-dilation and post-dilation configurations, respectively, according to an embodiment of the invention.

FIG. 4A depicts a further embodiment of a support frame 120 for use with a prosthetic heart valve according to the invention. The support frame 120 is generally circular and defines an inner diameter 122a, and has a generally rigid core 124 formed from a single core element 126 which is bent or otherwise formed into a generally circular shape with opposing ends 128a, 128b which meet and connect at an overlapping section 130 having a length 132a. The overlapping section 130 may include adhesive, solder, welds, mechanical connections, etc. in order to secure the overlapping ends 128a, 128b together. In the particular embodiment depicted, the overlapping section 130 has a ratchet-like assembly formed from interacting portions 134a, 134b at or adjacent the opposing ends 128a, 128b. The support frame 120 may include a covering (not shown) around the core 124.

Figure 4B:
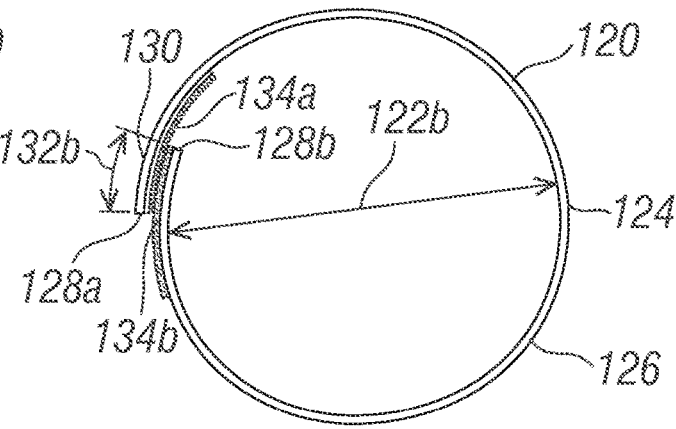

FIG. 4B depicts the support frame 120 of FIG. 4A after it has been subjected to a dilation force. The support frame 120 has been expanded to a larger inner diameter 122b, with the core 124 enlarged so that the overlapping section 130 is smaller, having a new shorter length 132b. The dilation force caused the interacting portions 134a, 134b to temporarily release their connection to permit the relative movement of the overlapping ends 128a, 128b, but with the dilation force removed the interacting portions 134a, 134b once again form a connection, so that the support frame 120 is again generally rigid. Note that, depending on the particular application, a support frame could be formed similar to that of FIGS. 4A-4B but with the interacting portions configured so that no fixed connection is formed between the overlapping ends after dilation, so that the support frame will be generally non-rigid after the dilation force has been applied. In such an embodiment, the support frame may be configured to provide (after dilation) an inward (compressive) force upon any expandable prosthetic valve that may be deployed within the valve orifice of the original (and now dilated) prosthetic valve. This inward compressive force may help to seat and otherwise hold the expandable prosthetic valve in its desired position within the native valve annulus and also within the now-dilated (prior) prosthetic valve.

Figure 5A:
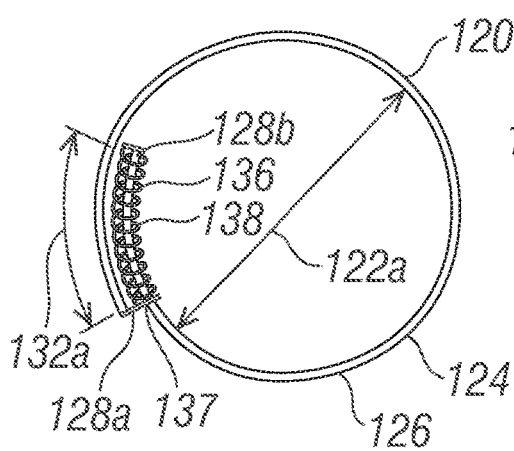
FIGS. 5A-5B depict top views of a prosthetic heart valve support structure in pre-dilation and post-dilation configurations, respectively, according to an embodiment of the invention.
Figure 5B:
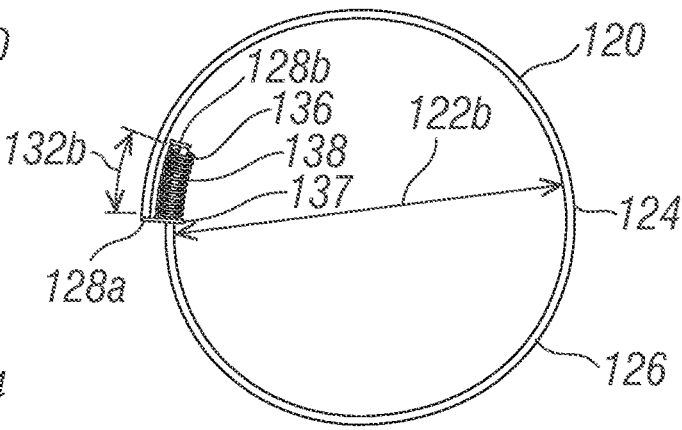

FIGS. 5A-5B depict a further embodiment of a support frame 120 for use with a prosthetic heart valve according to the invention. The support frame 120 is similar to that depicted in FIG. 4A, except the overlapping section 130 includes a sliding mechanical connection 136 having a slot 137 secured to one opposing end 128a, the second opposing end 128b having been passed through the slot 137 to form the overlapping section 130, and also including a spring 138 extending from the slot 137 to the second opposing end 128b. The spring 138 permits expansion and/or contraction of the support frame 120, with the spring 138 generally biasing the support frame 120 toward a smaller diameter, such as the smaller inner diameter 122a of FIG. 5A, but also permitting the support frame 120 to be expanded, when subject to an outside force such as a dilation balloon and/or expandable prosthetic valve, to a larger diameter such as the inner diameter 122b of FIG. 5B. Note that the spring 138 can also permit the support frame 120 (and associated valve annulus) to move with physiological annular dynamic motion, e.g., to make smaller expansions and/or contractions in response to normal valve function/heart movement as the patient's heart beats and pumps blood through the valve. The support frame 120 may include a covering (not shown) around the core 124. The support frame 120 may be formed of various materials, including elgiloy. The spring 138 can be configured to provide a specific force in opposing expansion of the support frame 120, and may be configured so that the force provided is insufficient to oppose the dilation force from a dilation balloon and/or expandable stent which might be expanded within the support frame 120. The spring 138 could be formed from traditional coil springs, compressible materials, pleated sewing rings, accordion sewing rings, and other configurations configured to provide a spring-like force.

Figure 6E:
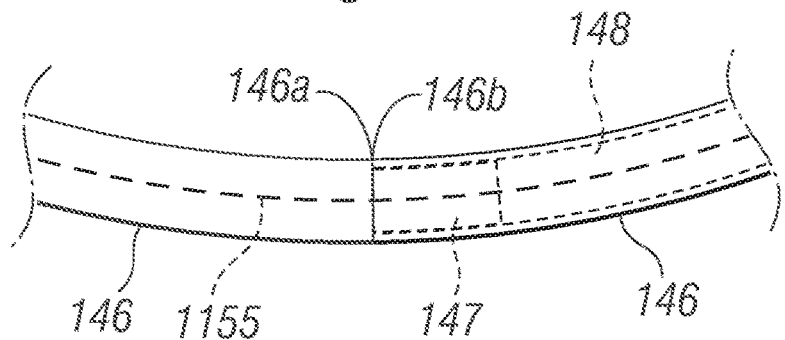
FIGS. 6E and 6F depict close-up top views of a portion, in expanded and unexpanded configurations, respectively, of a prosthetic heart valve support structure according to an embodiment of the invention.

In another embodiment of the invention, a prosthetic heart valve includes a support frame having a rigid and/or expansion-resistant core configured to separate into a plurality of pieces when subjected to a dilation force. Such a rigid and/or expansion-resistant core could be formed as a single piece, which might include one or more weak points that are subject to separation when subjected to a dilation force. In one embodiment a rigid and/or expansion-resistant core could be formed from a plurality of segments positioned in edge-to-edge fashion and configured to separate when subjected to a dilation force. FIGS. 6A-6C depict one such embodiment of a support frame 140 for use with a prosthetic heart valve according to the invention. The support frame 140 is generally circular (although other shapes are within the scope of the invention) and defines an orifice 141 having an inner diameter 142a, and has a generally rigid and/or expansion-resistant core 144 formed from multiple core segments 146 which are arranged in edge-to-edge fashion to form the generally circular shape of the core 144. Each segment 146 has an inner lumen 148, with the segments 146 when assembled into the core 144 forming a continuous core lumen 150.

Adjacent segments 146 join at seams 152, which may include adhesive, solder, welds, etc. in order to secure and/or seal the seam 152 between the adjacent segments 146. The support frame 140 has a pre-dilation cord 154 and a post-dilation cord 156 passing through the core lumen 150. The pre-dilation cord 154 may be a generally inelastic cord which is sufficiently tight to hold adjacent segments together and to prevent unwanted dilation of the support frame 140. A covering (not shown) may also be included to cover the core 144. The covering may be formed of cloth, and may be elastic.

Both the seams 152 and pre-dilation cord 154 are configured to fail or stretch when subjected to a dilation force, such as that provided by a dilation balloon, whereupon the support frame 140 will assume the expanded configuration depicted in FIG. 6D, with an enlarged inner diameter 142b. For example, the pre-dilation cord 154 may be an inelastic cord configured to fail when subject to a selected force, such as 1, 2, 3, 4, or more atmospheres, which are within the range of forces provided by many dilation balloons used in percutaneously-deployed heart valve procedures. In one embodiment, the seams 152 are merely sealed, with the sealant providing little if any securement against separation of adjacent segments 146. In such an embodiment, the pre-dilation cord 154 may serve as the sole device to hold the core segments 146 together in the rigid and/or expansion-resistant (pre-dilation) configuration. Once the pre-dilation cord 154 fails or stretches due to the dilation pressure, essentially all of the seams 152 will separate so that adjacent segments 146 separate with spaces 158 separating the adjacent segments 146. The remaining portions of the pre-dilation cord 154 remain within the support frame 140 after dilation.

The post-dilation cord 156 remains intact after dilation and may serve to hold the support frame 140 together post-dilation. The post-dilation cord 156 could be elastic, and/or could be inelastic and have a larger diameter, and possibly a higher failure strength, than the pre-dilation cord 154. If the post-dilation cord 156 is elastic, it may provide an inward compressive force into the central orifice 141. If the post-dilation cord 156 is generally inelastic, it will remain intact after dilation either because its strength was too great to be ruptured by the dilation balloon or because it had a diameter that was larger than that of the inflated dilation balloon.

In a variation of the embodiment of FIGS. 6A-6D, the pre-dilation cord 154 could be left out of the support frame 140, and the seams 152 themselves could have adhesive or other connections that serve to hold the segments 146 together prior to dilation. In a further variation, the pre-dilation cord 154 could be left out of the support frame, with a post-dilation cord 156 configured to be elastic and with sufficient strength/elasticity to provide an inward compressive force into the central orifice with sufficient strength to hold the segments 146 together prior to dilation, but with the inward compressive force weak enough to permit the support frame 140 to be dilated and to permit an expandable prosthetic heart valve to be deployed therein. Accordingly, the post-dilation cord 156 would serve as both pre-dilation cord and post-dilation cord.

Visualization references (such as the visualization markers 73 from FIGS. 2A-2D) may be included on or in various portions of the device. For example, visualization references may be placed on, in, or adjacent the support frame 140, core 144, segments 146, pre-dilation cord 154, and/or post-dilation cord 156, etc. in the device of FIGS. 6A-6D. Such visualization references can help a user to properly position a dilation balloon and/or subsequently-deployed expandable prosthetic heart valve within the previously-deployed prosthetic heart valve having the support frame 140. For example, visualization markers positioned at the generally rigid support frame 140 (or more specifically at the segments 146 and/or the pre-dilation cord 154 and/or post-dilation cord 156) could be used to guide delivery and expansion of a dilation balloon, and also to confirm that the support frame 140 has been dilated. The visualization markers could also be used to guide delivery and expansion of the expandable prosthetic heart valve within the support frame 140, and to confirm proper deployment of the expandable prosthetic heart valve.

Figure 6F:
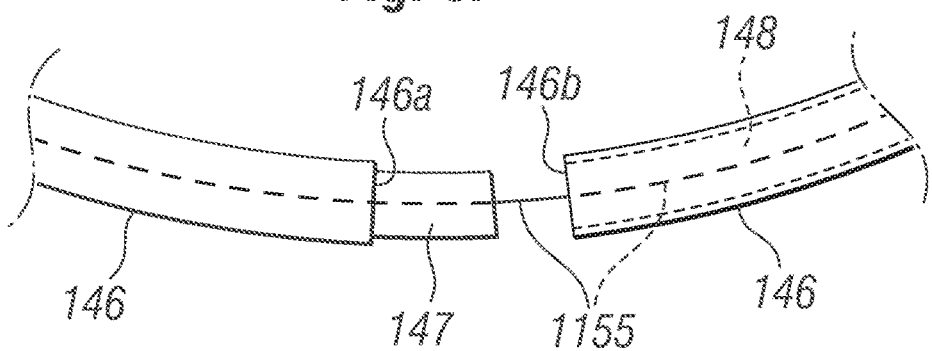

The support frame 140 may have segments 146 having ends 146a, 146b which interlock and/or otherwise interact in order to hold the segments 146 together and/or in alignment. As depicted in the close-up view of FIG. 6E, adjacent segments 146 may include interconnecting ends 146a, 146b, with one end 146a having a member 147 configured to be received within the lumen 148 or other opening in an end 146b of an adjacent segment 146. The interconnecting ends 146a, 146b keep the adjacent segments 146 in a desired alignment so that the segment ends 146a, 146b cannot slide sideways with respect to the member 147 and lumen 148, but does permit the segments 146 to be pulled apart, as depicted in FIG. 6F, in order to permit expansion of the support frame 140 (as was depicted in FIG. 6D). The pulling apart of the segments 146 may be opposed by various structures set forth herein which oppose and/or restrict dilation of a support frame, such as one or more elastic and/or inelastic cords 155 configured to oppose and/or restrict dilation of the support frame as was depicted in FIGS. 6A-6D.

Figure 7A:
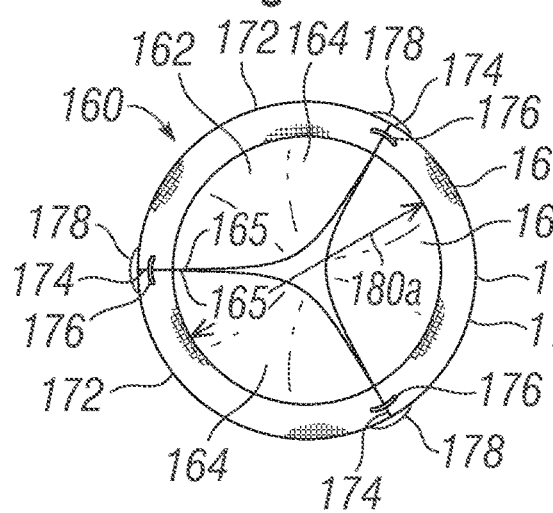
FIGS. 7A and 7B depict top views of unexpanded and expanded configurations, respectively, of a prosthetic heart valve support structure according to an embodiment of the invention.
Figure 7B:
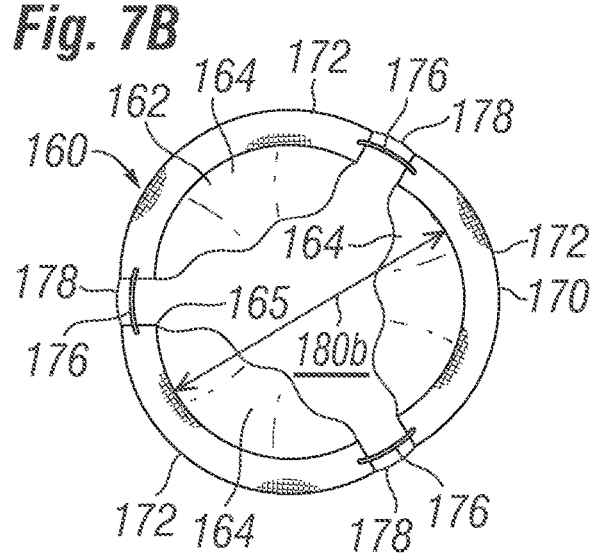

FIGS. 7A-7B depict a further embodiment of the invention, with a prosthetic heart valve 160 having a valve structure 162 formed from three (3) leaflets 164 spaced around the valve orifice 166. The support frame 168 includes a core 170 formed from three (3) segments 172. At the base/perimeter of the valve structure 162, the edges 165 of each leaflet 164 coincide with the edges of each respective segment 172 as well as the seams 174 (and the commissure supports, if present). Adjacent segments 172 are connected to each other at the seams 174, such as with adhesive(s), weld(s), etc., in order to form the rigid and/or expansion-resistant (pre-dilation) support frame 168. Adjacent segments 172 are also connected via individual inelastic cords 176 and elastic cords 178 extending between the adjacent segments 172. As depicted in FIG. 7A, the (pre-dilation) prosthetic valve 160 has a valve orifice 166 having an inner diameter 180a. A cloth cover (not shown) or similar covering will also typically be included to cover the support frame 168 and its associated elements (e.g., inelastic cords 176 and elastic cords 178).

When the prosthetic heart valve 160 of FIG. 7A is subjected to a dilation force, the seams 174 between the segments 172 will fail and the support frame 168 will separate into the three segments 172, as depicted in FIG. 7B. Note that in this particular embodiment the inelastic cords 176 do not serve to hold adjacent segments against each other, but instead permit adjacent segments to separate when subjected to a dilation force. The inelastic cords 176 prevent excessive separation between any adjacent segments 172 as the dilation balloon (or other dilation force) is applied, with the result being that the segments 172 will all be spaced generally equally apart from each other once the full dilation force is applied. After the dilation force is removed, the elastic cords 178 will serve to pull the adjacent segments toward each other and to provide a generally inward (compressive) pressure to the valve orifice 166 but while also maintaining the post-dilation inner diameter 180b (FIG. 7B) at a larger size than the pre-dilation diameter 180a (FIG. 7A). Because the leaflets 164 were positioned with their base edges coinciding with the seams 174 between segments 172, the leaflets 164 can remain generally intact after dilation and still permit the segments 172 to separate to form the enlarged inner diameter 180b. Note, however, that deploying a new expandable prosthetic valve within the prosthetic heart valve 160 will generally involve deploying an expandable heart valve support stent that will crush the leaflets 164 of the current prosthetic heart valve 160 against the support frame 168, walls of the native valve annulus, and/or lumen.

If the prosthetic heart valve 160 includes commissure supports (not shown) on the support frame 168, the commissure supports can be positioned on or adjacent the seams 174 between segments 172, and the commissure supports can also be configured to split lengthwise when the prosthetic heart valve 160 is dilated so that one-half of each commissure support will remain with the adjacent segment 172 on either side of said commissure support. In such an embodiment, the edges of the valve leaflets 164 can be secured (e.g., during assembly of the prosthetic heart valve 160) to the respective half of each commissure support, so that when the prosthetic heart valve 160 is dilated adjacent leaflets 164 can separate from adjacent leaflets 164, but each leaflet 164 will still remain secured via its edges to its respective commissure support halves.

There are many variations of the above-cited embodiments, including various combinations of the various embodiments. For example, the pre-dilation cord 154 and/or post-dilation cord 156 of FIGS. 6A-6D could be used with the core 100 of FIGS. 3A-3D in order to provide inward compressive force after the core 100 was dilated. The post-dilation cord 156 of FIGS. 6A-6D could be replaced by a cover 108 such as that depicted in FIGS. 3A-3D, with the cover 108 serving to hold the post-dilation core assembly (including any segments and/or pieces thereof) together and also (if formed form elastic material) providing an inward compressive force to the valve orifice.

Figures 8A, 9A:
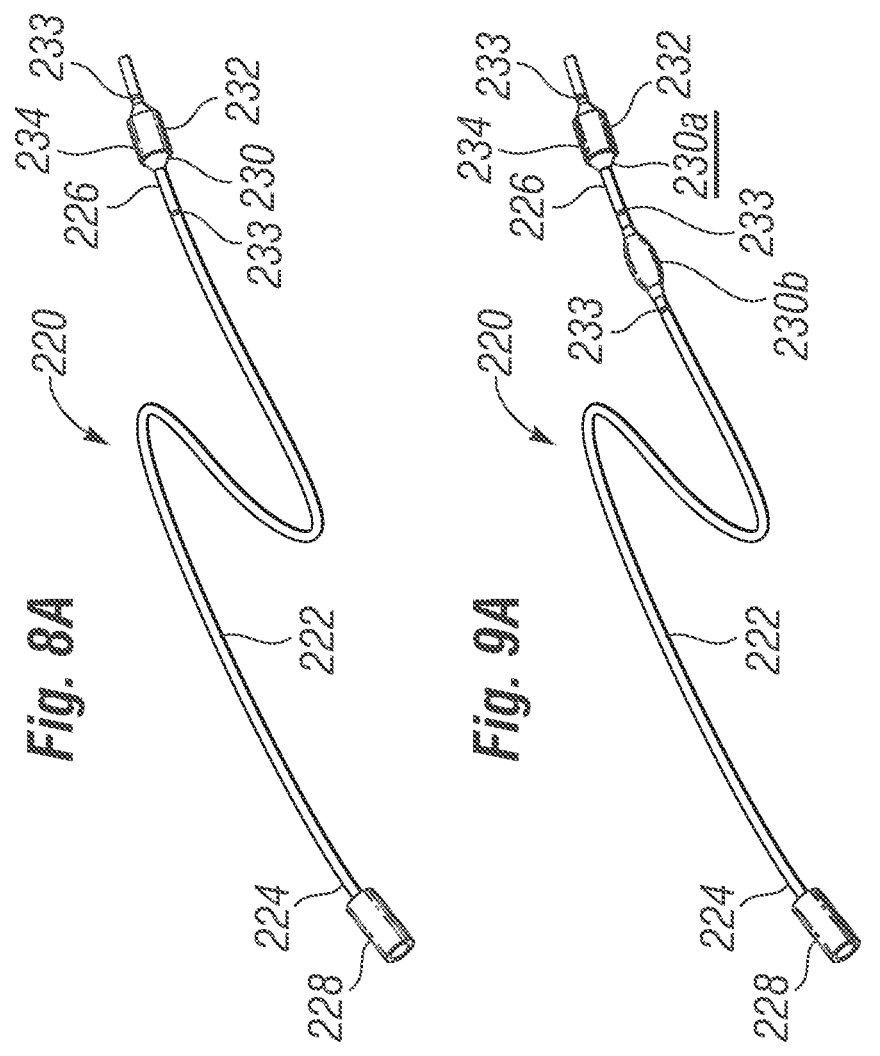

FIG. 8A depicts an expandable prosthetic heart valve deployment catheter 220 configured for (prior) prosthetic heart valve dilation and (replacement) expandable prosthetic heart valve deployment. The deployment catheter 220 has an elongated main body 222, a proximal end 224, and a distal end 226. The proximal end 224 includes a handle 228. The distal end 226 includes a dilation balloon 230 upon which an expandable prosthetic valve 232 is mounted. In the particular embodiment depicted, the expandable prosthetic valve 232 includes a stent 234. The distal end 226 may also include one or more radiopaque markers 233 or similar visibility markers to improve visibility of the device within the patient when using fluoroscopy or other viewing technologies.

Figure 8D:
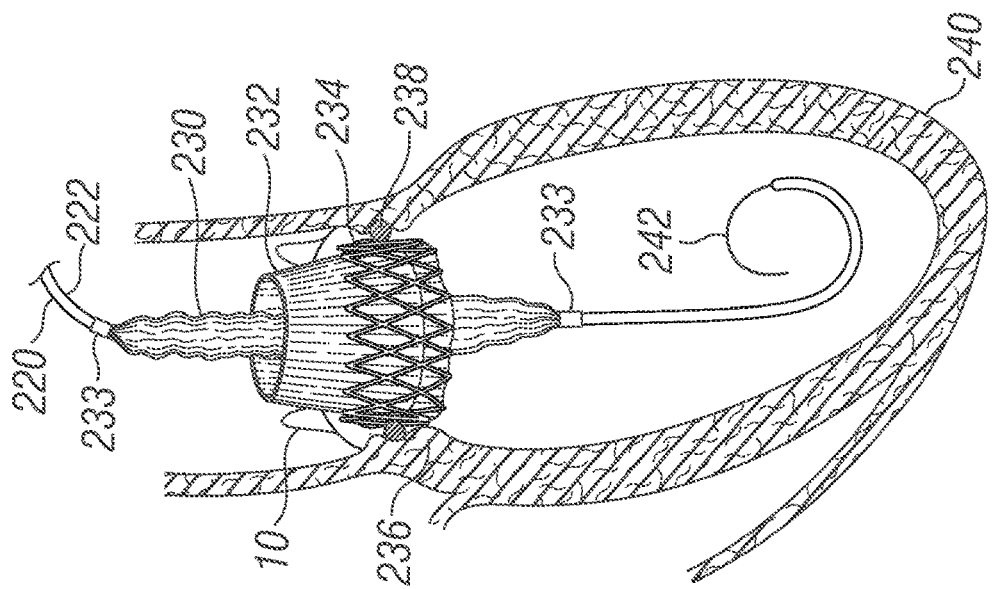
FIG. 8D depicts the expandable prosthetic heart valve deployment catheter of FIG. 8A being withdrawn from the patient according to an embodiment of the invention.
Figure 8C:
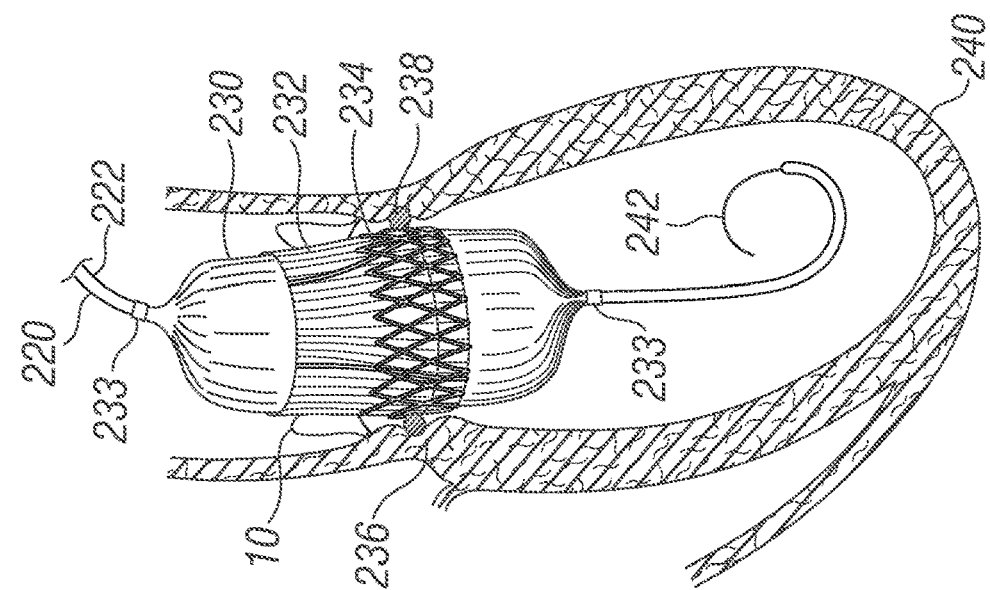
FIG. 8C depicts the expandable prosthetic heart valve deployment catheter of FIG. 8A dilating the previously-deployed prosthetic heart valve and deploying an expandable prosthetic heart valve therewithin according to an embodiment of the invention.
Figure 8B:
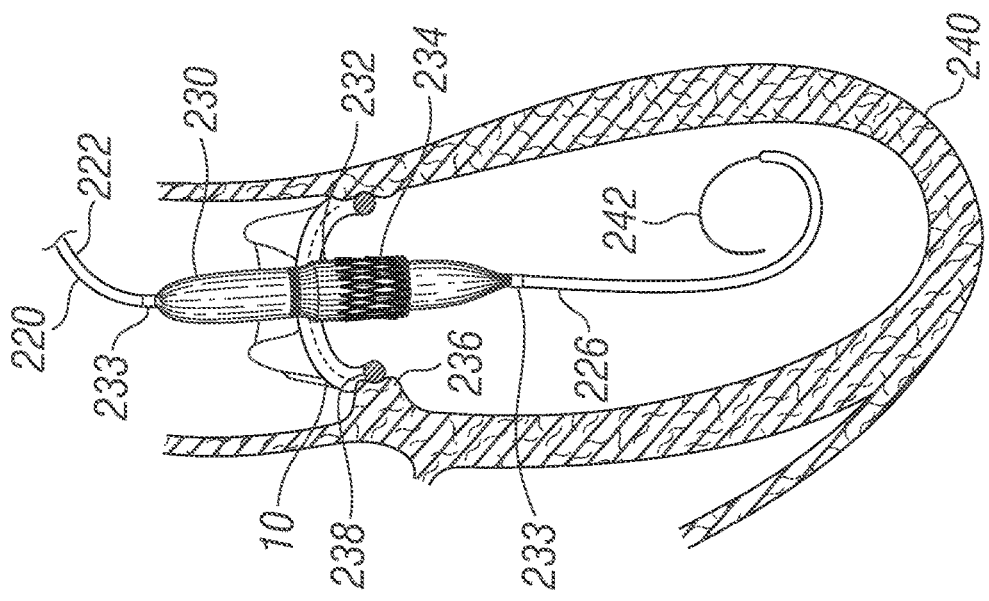
FIG. 8B depicts the expandable prosthetic heart valve deployment catheter of FIG. 8A positioned within a previously-deployed prosthetic heart valve in a heart valve annulus of a patient according to an embodiment of the invention.

FIGS. 8B-8D depict deployment of an expandable prosthetic heart valve 232 within a heart valve annulus 236 where a prosthetic heart valve 10 has previously been deployed. The previously-deployed prosthetic heart valve 10 may have been deployed using any methods, including methods currently known in the art such as traditional (open chest) surgery, minimally-invasive (e.g., keyhole) surgery, and percutaneous surgery. Depending on the particular application, the previously-deployed prosthetic heart valve 10 can be deployed in the patient years prior to, days prior to, hours prior to, or immediately prior to deployment of the expandable prosthetic heart valve 232 as depicted in FIGS. 8B-8D.

FIG. 8B depicts the expandable prosthetic heart valve deployment catheter 220 of FIG. 8A with the distal end 226 advanced so that the dilation balloon 230 and expandable prosthetic heart valve 232 are positioned within the previously-deployed prosthetic heart valve 10 in the patient's heart 240. The previously-deployed prosthetic heart valve 10 is seen in cross-section to show the generally rigid and/or expansion-resistant support frame 238.

In the particular embodiment depicted in FIG. 8B, the deployment catheter 220 has been advanced over a guide wire 242, which was advanced into the patient's heart 240 and previously-deployed prosthetic heart valve 10 prior to advancement of the deployment catheter 220 into the patient. Note that the use of a guide wire 242 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 8C, once the dilation balloon 230 and expandable prosthetic heart valve 232 are properly positioned within the heart valve annulus 234 and previously-deployed prosthetic heart valve 10, the dilation balloon 230 is expanded. The expanding dilation balloon 230 forces the stent 234 to expand outwardly, and crushes the leaflets 244 of the previously-deployed prosthetic heart valve 10 against the heart valve annulus 236. The force from the expanding dilation balloon 230 also dilates the previously-deployed prosthetic heart valve 10 and heart valve annulus 236, forcing the support frame 238 of the previously-deployed prosthetic heart valve 10 to expand and/or become non-rigid.

In FIG. 8D, the dilation balloon 230 is deflated or otherwise reduced in diameter, with the new expandable prosthetic valve 232 deployed in the heart valve annulus 236 and previously-deployed prosthetic heart valve 10, and also held in place by the stent 234. The outward pressure from the expanded stent 232, along with the inward pressure from the heart valve annulus 236 and from any elastic portions (such as core, cords, and/or or covers) of the previously-deployed prosthetic heart valve 10 or from the now-crushed previously-deployed prosthetic heart valve leaflets 244, combine to firmly seat the new expandable prosthetic valve 232 in the desired position in the heart valve annulus 236 and previously-deployed prosthetic heart valve 10. The deployment catheter 220 with the dilation balloon 230 can then be withdrawn from the heart 240, leaving the new expandable prosthetic heart valve 232 in its deployed position within the patient and the previously-deployed prosthetic heart valve 10.

In a further embodiment of the invention, the previously-deployed prosthetic heart valve 10 is dilated in a separate step from deployment of the expandable prosthetic heart valve 232. FIG. 9A depicts an expandable prosthetic heart valve deployment catheter 220 configured for previously-deployed prosthetic heart valve dilation and expandable prosthetic heart valve deployment using two separate balloons, and more specifically a distal balloon 230a and a proximal balloon 230b. The distal balloon 230a is configured to deploy the new expandable prosthetic valve 232, which is positioned on the distal balloon 230a, whereas the proximal balloon 230b is configured for dilation of the previously-deployed prosthetic heart valve 10.

FIGS. 9B-9D depict dilation of the previously-deployed prosthetic heart valve 10 and valve annulus 236 using the proximal balloon 230b. In FIG. 9B, the deployment catheter 220 has been advanced into the heart 230 with the distal balloon 230a (with expandable prosthetic valve 232 thereon) advanced past the previously-deployed prosthetic heart valve 10, and the proximal balloon 230b positioned within the previously-deployed prosthetic heart valve 10 and valve annulus 236.

The proximal balloon 230b is inflated or otherwise expanded, as depicted in FIG. 9C, thereby dilating the previously-deployed prosthetic heart valve 10 and valve annulus 236. The support frame 238 of the previously-deployed prosthetic heart valve 10 is expanded and/or assumes a generally non-rigid configuration, similarly to the changes previously discussed with respect to the dilation discussed in FIG. 8C above.

After dilation of the previously-deployed prosthetic heart valve 10, the proximal balloon 230b is deflated or otherwise reduced in diameter, as depicted in FIG. 9D. The deployment catheter 220 may then be withdrawn from the patient until the proximal balloon 230b is proximal of the previously-deployed prosthetic heart valve 10 and the distal balloon 230a is positioned within the previously-deployed prosthetic heart valve 10. The distal balloon 230a will be positioned within the previously-deployed prosthetic heart valve 10 in a similar fashion to that depicted for balloon 230 in FIG. 8B. The distal balloon 230a will then be expanded to deploy the expandable prosthetic valve 232 in essentially the same manner as was discussed and depicted in FIGS. 8B-8D. The distal balloon 230a will serve to deploy the new expandable prosthetic valve 232, and may also serve to further dilate the previously-deployed prosthetic heart valve 10 and/or native valve annulus 236.

Note that the expandable prosthetic valve may be self-expanding, in which case the deployment catheter may not have a dilation balloon as depicted in FIGS. 8A-8D and 9A-9D. Moreover, such a self-expanding prosthetic heart valve could be deployed with or without prior dilation of the previously-deployed prosthetic heart valve. For example, a self-expanding prosthetic heart valve may provide sufficient outward radial force to dilate the previously-deployed prosthetic heart valve and/or to hold a now-dilated previously-deployed prosthetic heart valve in an expanded configuration in order to provide sufficient room for the self-expanding prosthetic heart valve in its expanded configuration.

With reference to FIG. 10, an annuloplasty ring device 1010 according to the invention is depicted in a heart 12. In the particular embodiment depicted, the annuloplasty ring 1010 is deployed in the mitral valve 1050, and more particularly is secured (via, e.g., sutures) adjacent and around the mitral valve annulus 64. The mitral valve 1050 has two leaflets (anterior leaflet 1054a and posterior leaflet 1054p), lower portions and free edges 1056 of which are connected via mitral chordae tendineae 1058 to papillary muscles 60 in the left ventricle 20 for controlling the movements of the mitral valve 1050. The annuloplasty ring 1010 provides a desired shape to the mitral valve annulus 64, thereby providing proper alignment and closure of the mitral valve leaflets 1054a, 1054p.

Figure 11A:
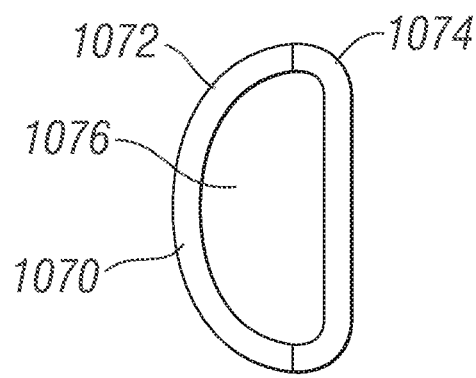
FIG. 11A depicts a top view of an annuloplasty ring according to an embodiment of the invention.

FIG. 11A depicts a top view of an annuloplasty ring 1070 according to an embodiment of the invention, where the annuloplasty ring 1010 is generally "D"-shaped and has a generally rigid portion 1072 and generally flexible portion 1074. In the particular embodiment depicted in FIG. 11A, the generally rigid portion 1072 is generally curved, but the generally flexible portion 1074 is generally straight.

Figure 11B:
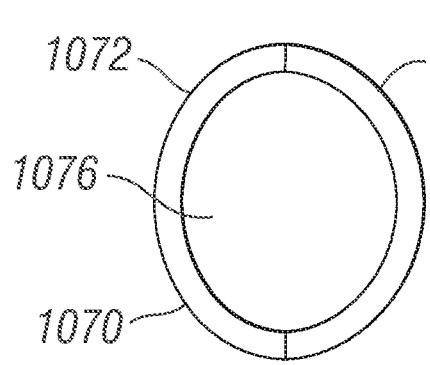
FIG. 11B depicts a top view of the annuloplasty ring of FIG. 11A after the annuloplasty ring has been dilated.

When the annuloplasty ring 1070 of FIG. 11A is subjected to a dilation force (such as that from a dilation balloon), the annuloplasty ring 1070 will transition from the generally "D"-shaped configuration of FIG. 11A to the generally circular shape of FIG. 11B. While the generally rigid portion 1072 has remained generally unchanged in shaped (i.e., is still generally curved), the generally flexible portion 1074 has transitioned from the generally straight configuration of FIG. 11A to the generally curved configuration of FIG. 11B. The overall result is that the "post-dilation" annuloplasty ring 1070 of FIG. 11B has a generally circular opening 1076 when viewed from the top.

Figure 12A:
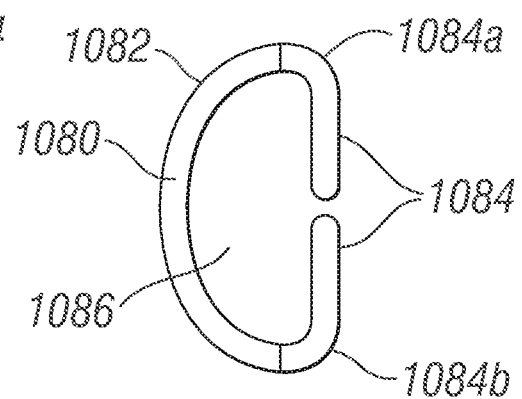
FIG. 12A depicts a top view of an annuloplasty ring according to a further embodiment of the invention.

FIG. 12A depicts a top view of an annuloplasty ring 1080 according to a further embodiment of the invention, where the annuloplasty ring 1080 is generally "D"-shaped and has a generally rigid portion 1082 and a generally flexible portion 1084 which has two separate generally flexible portions 1084a, 1084b. The annuloplasty ring 1080 of FIG. 12A is accordingly discontinuous in structure (as opposed to the continuous structure of FIGS. 11A-11B). In the particular embodiment depicted in FIG. 12A, the generally rigid portion 1082 is generally curved, but each of the generally flexible portions 1084a, 1084b are generally straight and are also generally aligned so that the generally flexible portion 1084 is generally straight.

Figure 12B:
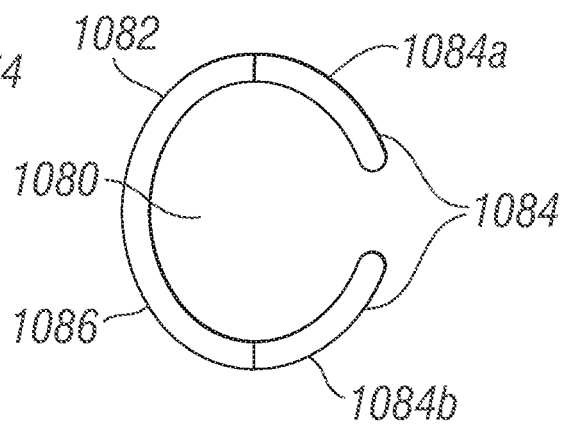
FIG. 12B depicts a top view of the annuloplasty ring of FIG. 12A after the annuloplasty ring has been dilated.

When the annuloplasty ring 1080 of FIG. 12A is subjected to a dilation force (such as that from a dilation balloon), the annuloplasty ring 1080 will transition from the generally "D"-shaped configuration of FIG. 12A to the generally circular (but still discontinuous) shape of FIG. 12B. While the generally rigid portion 1082 has remained generally unchanged in shaped (i.e., is still generally curved), the generally flexible portions 1084a, 1084b have transitioned from the generally straight configurations of FIG. 12A to the generally curved configurations of FIG. 12B. The overall result is that the "post-dilation" annuloplasty ring 1080 of FIG. 12B is generally circular but discontinuous when viewed from the top, providing a generally circular opening 1086.

Figure 13A:
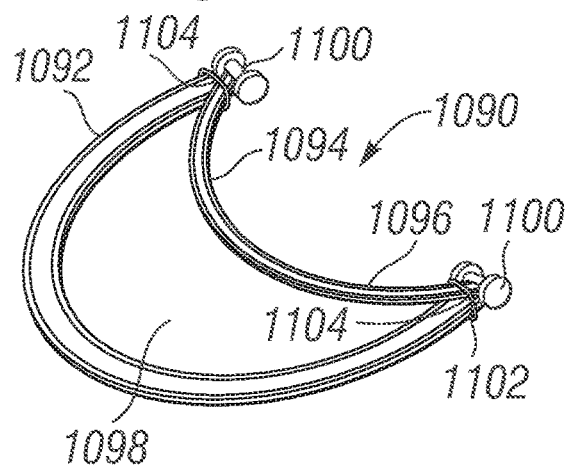
FIGS. 13A and 13B depict perspective and top views, respectively, of an annuloplasty ring according to a further embodiment of the invention.
Figure 13C:
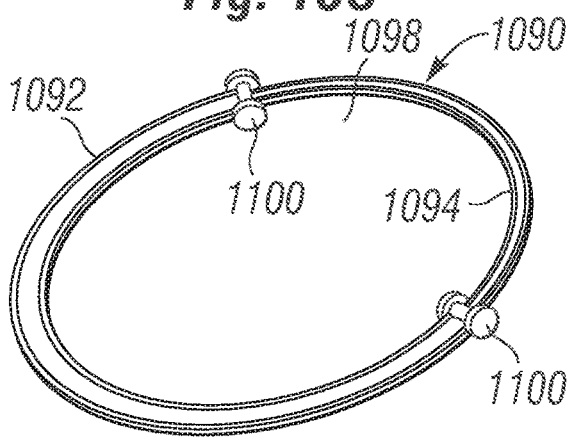
FIGS. 13C and 13D depict perspective and top views, respectively, of the annuloplasty ring of FIGS. 13A and 13B after the annuloplasty ring has been dilated.
Figure 13B:
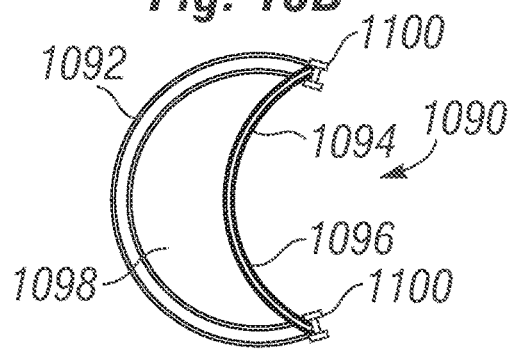
Figure 13D:
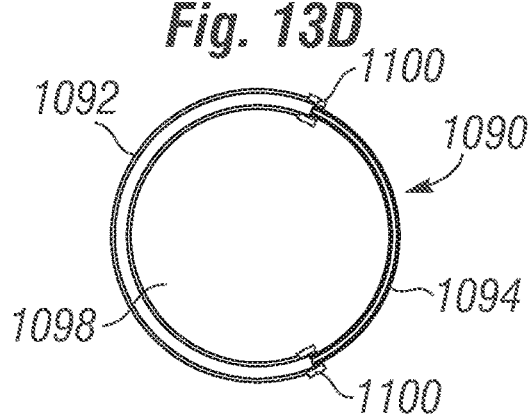

FIGS. 13A-13D depict a further embodiment of the invention, where an annuloplasty ring 1090 has a first generally rigid portion 1092 and second generally rigid portion 1094. As depicted in FIGS. 13A-13B, the annuloplasty ring 1090 in its pre-dilation configuration is generally D-shaped, with the second generally rigid portion 1094 being shorter than the first generally rigid portion 1092. The second generally rigid portion 1092 defines a curve 1096 which is directed inward with respect to the ring opening 1098.

The first generally rigid portion 1092 and second generally rigid portion 1094 of the annuloplasty ring 1090 are held together via a movable connection, which in the particular embodiment is formed by two hinges 1100 secured to either end of the first generally rigid portion 1092 and second generally rigid portion 1094. The hinges 1100 permit the second generally rigid portion 1094 to rotate relative to the first generally rigid portion 1092 when an outward force, such as that provided from an expanded dilation balloon, is applied to the annuloplasty ring 1090. When the second generally rigid portion 1094 is rotated relative to the first generally rigid portion 1092 responsive to such an outward force, the annuloplasty ring 1090 will transform from the generally D-shaped configuration of FIGS. 13A-13B to the generally circular configuration of FIGS. 13C-13D.

In order to prevent unwanted rotation of the second generally rigid portion 1094 with respect to the first generally rigid portion 1092, a lock or other restraint 1102 is provided. The restraint 1102 prevents rotation of the second generally rigid portion 1094 with respect to the first generally rigid portion 1092 prior to application of a dilatation force. However, the restraint 1102 is configured to fail or open or otherwise release upon application of a significant dilation force (such as that provided by a dilation balloon) to permit movement (which in the particular embodiment depicted is in the form of rotation) of the second generally rigid section 1094 with respect to the first generally rigid section 1092 when the annuloplasty ring 1090 is subjected to the dilation force.

In the particular embodiment of FIG. 13A, the restraint 1102 comprises lines of suture 1104 tied between the first generally rigid portion 1092 and second generally rigid portion 1094. Other types of restraints are also within the scope of the invention, including elastically deformable materials and/or structures such as springs, and plastically deformable materials (including breakable materials) such as suture, metals, plastics, etc.

Figure 14A:
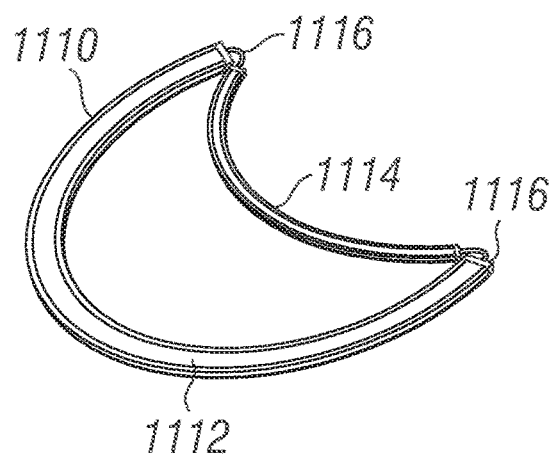
FIG. 14A depicts a perspective view of an annuloplasty ring according to a further embodiment of the invention.
Figure 14B:
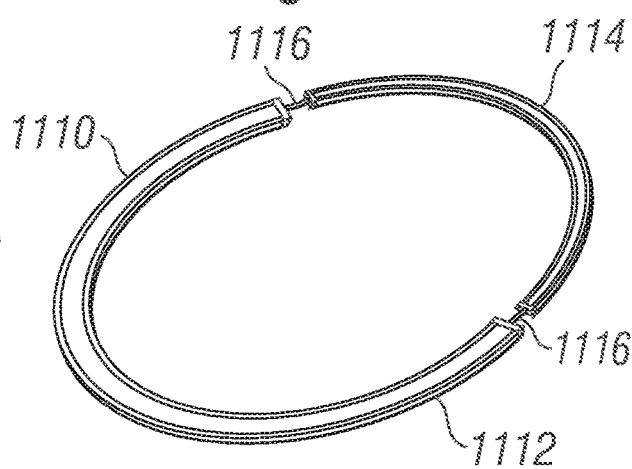
FIG. 14B depicts a perspective view of the annuloplasty ring of FIG. 14A after the annuloplasty ring has been dilated.

In a further embodiment of the invention depicted in FIGS. 14A-14B, the annuloplasty ring 1110 has a restraint 1116 that is a plastically deformable material (e.g., a bendable metal) that prevents relative movement/rotation of the two generally rigid sections 1112, 1114 prior to application of the dilation force, but upon application of the dilation force permits relative rotational or other movement while still providing a connection between the sections 1112, 1114. The restraint 1116 may be a wire-like connection that can be bent to a desired shape in order to permit the two generally rigid sections 1112, 1114 to rotate relative to each other.

FIG. 15A depicts a prosthetic heart valve deployment catheter 1120 configured for annuloplasty ring dilation and prosthetic heart valve deployment. The deployment catheter 1120 has an elongated main body 1122, a proximal end 1124, and a distal end 1126. The proximal end 1124 includes a handle 1128. The distal end 1126 includes a dilation balloon 1130 upon which an expandable prosthetic valve 1132 is mounted. In the particular embodiment depicted, the prosthetic valve 1132 includes a stent 1134. The distal end 1126 may also include one or more radiopaque markers 1133 or similar visibility markers to improve visibility of the device within the patient when using fluoroscopy or other viewing technologies.

FIGS. 15B-15D depict deployment of a prosthetic heart valve 1132 within a heart valve annulus 1136 for a heart valve 1138 where an annuloplasty ring 1010 has previously been deployed. The annuloplasty ring 1010 may have been deployed using any methods, including methods currently known in the art such as traditional (open chest) surgery, minimally-invasive (e.g., keyhole) surgery, and percutaneous surgery. The annuloplasty ring 1010 encircles the heart valve 1138. Depending on the particular application, the annuloplasty ring 1010 can be deployed in the patient years prior to, days prior to, hours prior to, or immediately prior to deployment of the prosthetic heart valve 1132 as depicted in FIGS. 15B-15D.

FIG. 15B depicts the prosthetic heart valve deployment catheter 1120 of FIG. 15A with the distal end 1126 advanced so that the dilation balloon 1130 and expandable prosthetic heart valve 1132 are positioned within the heart valve 1138 in the patient's heart 1140. The annuloplasty ring 1010 is seen in cross-section, with a cross section of the ring first portion 1010a at the right side of the valve annulus 1136, and a cross section of the ring second portion 1010b at the left side of the valve annulus 1136. Note that the ring second portion 1010b is depicted as extending somewhat more inward with respect to the valve annulus 1134, which might be the case where the ring 1010 is generally D-shaped and otherwise similar to that depicted in FIGS. 11A-11B and 13A-13C, with the ring first portion 1010a corresponds to ring portions 1072 (FIG. 11A), 1092 (FIG. 13A), and the ring second portion 1010b corresponds to ring portions 1074 (FIG. 11A), 1094 (FIG. 13A), respectively.

In the particular embodiment depicted in FIG. 15B, the deployment catheter 1120 has been advanced over a guide wire 1142, which was advanced into the patient's heart 1140 and heart valve 1138 prior to advancement of the deployment catheter 1120 into the patient. Note that the use of a guide wire 1142 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 15C, once the dilation balloon 1130 and prosthetic heart valve 1132 are properly positioned within the heart valve annulus 1134, the dilation balloon 1130 is expanded. The expanding dilation balloon 1130 forces the stent 1134 to expand outwardly, and crushes the native valve leaflets 1144 against the heart valve annulus 1136. The force from the expanding dilation balloon 1130 dilates the heart valve annulus 1136, and also forces the annuloplasty ring 1010 to expand and/or assume a more circular shape, which in the particular embodiment depicted involves displacing the ring second portion 1010b outward to a much greater extent than the outward movement of the ring first portion 1010a.

In FIG. 15D, the dilation balloon 1130 is deflated or otherwise reduced in diameter, with the prosthetic valve 1132 deployed in the heart valve annulus 1136 and held in place by the stent 1134. The outward pressure from the expanded stent 1132, along with the inward pressure from the heart valve annulus 1136, from the now-crushed native valves 1144, and/or from the now-dilated annuloplasty ring 1010, combine to firmly seat the prosthetic valve 1132 in the desired position in the heart valve annulus 1136. The deployment catheter 1120 with the dilation balloon 1130 can then be withdrawn from the heart 1140, leaving the prosthetic heart valve 1132 in its deployed position in the patient.

In a further embodiment of the invention, the native heart valve 1138 is dilated in a separate step from deployment of the prosthetic heart valve 1132. FIG. 16A depicts a prosthetic heart valve deployment catheter 1120 configured for annuloplasty ring dilation and prosthetic heart valve deployment using two separate balloons, and more specifically a distal balloon 1130a and a proximal balloon 1130b. The distal balloon 1130a is configured to deploy the prosthetic valve 1132, which is positioned on the distal balloon 1130a, whereas the proximal balloon 1130b is configured for dilation.

FIGS. 16B-16D depict dilation of the native valve 1138, valve annulus 1136, and annuloplasty ring 1010 using the proximal balloon 1130b. In FIG. 16B, the deployment catheter 1120 has been advanced into the heart 1130 with the distal balloon 1130a (with prosthetic valve 1132 thereon) advanced past the native heart valve 1138, and the proximal balloon 1130b positioned within the native heart valve 1138 and valve annulus 1136.

The proximal balloon 1130b is inflated or otherwise expanded, as depicted in FIG. 16C, thereby dilating the native valve 1138, valve annulus 1136, and annuloplasty ring 1010. The annuloplasty ring 1010 is expanded and/or assumes a more circular form, similarly to the changes previously discussed with respect to the dilation discussed in FIG. 15C above.

After dilation of the native valve 1138, the proximal balloon 1130b is deflated or otherwise reduced in diameter, as depicted in FIG. 16D. The deployment catheter 1120 may then be withdrawn from the patient until the proximal balloon 1130b is proximal of the valve annulus 1138 and the distal balloon 1130a is positioned within the valve annulus 1138. The distal balloon 1130a will be positioned within the valve annulus 138 in a similar fashion to that depicted for balloon 1130 in FIG. 15B. The distal balloon 1130a will then be expanded to deploy the prosthetic valve 1132 in essentially the same manner as was discussed and depicted in FIGS. 15B-15D. The distal balloon 1130a will serve to deploy the prosthetic valve 1132, and may also serve to further dilate the native valve native valve 1138, valve annulus 1136, and annuloplasty ring 1010.

Note that the expandable prosthetic valve may be self-expanding, in which case the deployment catheter may not have a dilation balloon as depicted in FIGS. 15A-15D and 16A-16D. Moreover, such a self-expanding prosthetic heart valve could be deployed with or without prior dilation of the annuloplasty ring. For example, a self-expanding prosthetic heart valve may provide sufficient outward radial force to dilate the annuloplasty ring and/or to hold the now-dilated annuloplasty ring in an expanded configuration in order to provide sufficient room for the self-expanding prosthetic heart valve in it expanded configuration.

Figure 17A:
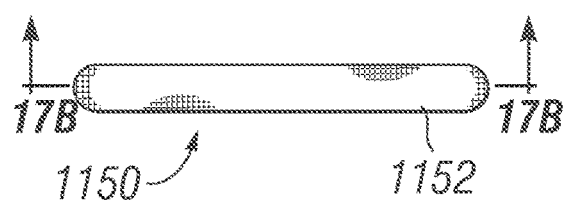
FIGS. 17A-17C depict side, top (in cross-section), and close-up sectional views, respectively, of an annuloplasty ring according to an embodiment of the invention.
Figure 17B:
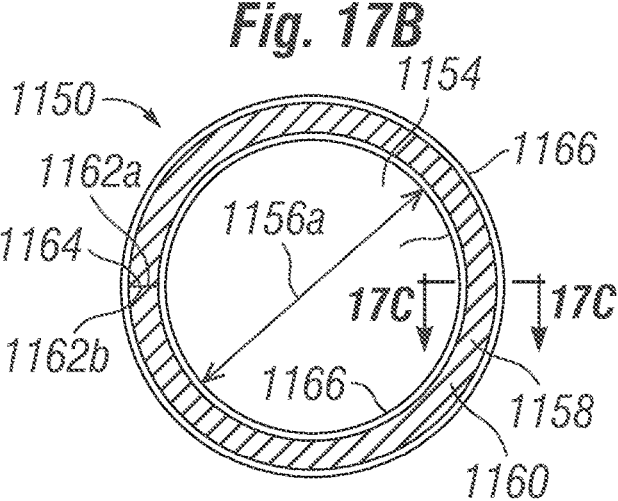
Figure 17C:
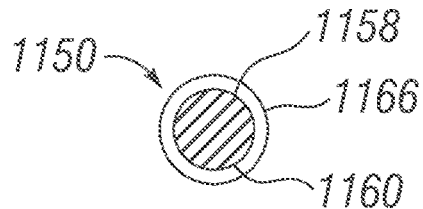

FIGS. 17A-17C depict an annuloplasty ring prosthetic heart valve 1150 having a support frame 1152 according to a further embodiment of the invention, with the annuloplasty ring 1150 having an orifice 1154 having an inner diameter 1156a. The support frame 1152 has a generally rigid and expansion-resistant core 1158 formed from a single core element 1160 which is bent or otherwise formed into a desired shape (which in the particular embodiment is generally circular) with opposing ends 1162a, 1162b meeting at a seam 1164 so as to form the complete loop around the annuloplasty ring 1150. The seam 1164 may include adhesive, solder, welds, etc. in order to secure the two ends 1162a, 1162b together. The annuloplasty ring 1150 includes a covering 1166 around the support core 1158. The covering 1166 may be a cloth-like material, and may be a sewing ring configured to be sewn to the native heart valve annulus during deployment of the annuloplasty ring 1150. The covering 1166 is generally flexible, and may be generally elastic. The covering 1166 (or a portion thereof) may also be generally compressible, especially in the portion facing inward toward the orifice 1154, which can assist in seating an expandable valve therein. A compressible material may be applied onto or within the covering 1166 in a position to provide a compressible region on the surface facing inward toward the orifice 1154.

Figure 17D:
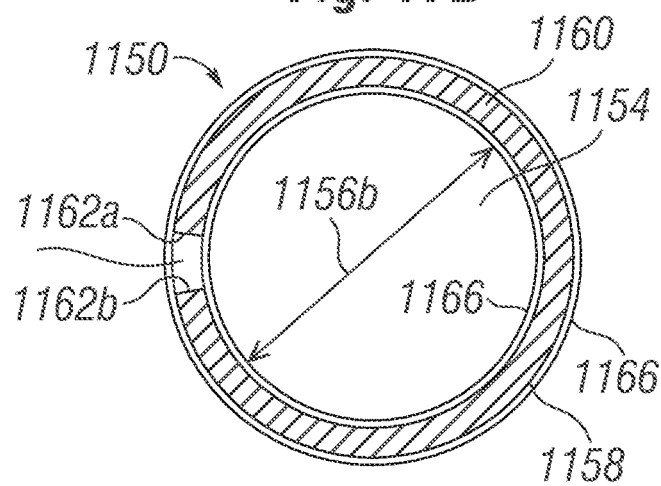
FIG. 17D depicts a top view, in cross-section, of the annuloplasty ring of FIGS. 17A-17C after the annuloplasty ring has been dilated.

When the annuloplasty ring 1150 is subject to a dilation force such as that from a dilation balloon catheter, the support frame 1152 will become non-rigid and expanded. More particularly, the seam 1164 of the core 1158 will rupture, so that the opposing ends 1162a, 1162b will be separated by an opening 1168, and the core 1158 will assume a generally C-shaped configuration as depicted in FIG. 17D. The covering 1166 will stretch or otherwise expand circumferentially to accommodate the enlarged/expanded core 1158, and the annuloplasty ring 1150 will have an enlarged inner diameter 1156b for the orifice 1154. Depending on the particular embodiment, including the particular construction of the core 1158 and/or covering 1166, the (post-dilation) annuloplasty ring 1150 may provide an inward (i.e., compressive) force toward the orifice 1154. For example, the core 1158 may be formed of a generally resilient spring-like material and/or memory material, and may be biased somewhat toward its non-dilated configuration (i.e., with the opposing ends 1162a, 1162b touching each other as in FIGS. 17A-17C). The covering 1166 may also (or alternatively) be elastic and, after dilation of the annuloplasty ring 1150, may provide an inward pull on the core 1160 so as to bias the opposing ends 1162a, 1162b toward each other. This inward pressure can help to seat an expandable heart valve that may be deployed within the annuloplasty ring 1150 and native heart valve. In an embodiment where compressible material is provided (e.g., as part of the covering 1166) facing inward toward the orifice 1154, then the compressible material can provide additional assistance in seating an expandable heart valve within the annuloplasty ring 1150.

In some procedures where an expandable prosthetic heart valve is used to replace a native valve that has a previously-deployed annuloplasty ring, it may be desirable for the expandable prosthetic heart valve to have a deployed (expanded) orifice having a cross-sectional area approximately equal to the orifice cross-sectional area of the native valve. Such consistency between orifice areas can be useful in maintaining proper blood flow, so that the expandable prosthetic heart valve will provide the same blood flow as was provided by the native heart valve. For example, Edwards Lifesciences has Sapien™ expandable prosthetic heart valves having outer diameters of 23 and 26 mm, respectively, which have corresponding inner diameters of about 20 and 23 mm, respectively, which correspond to orifice areas of about 315 and 415 square mm, respectively. Accordingly, the post-dilation orifice area of the native valve orifice with annuloplasty ring may be on the order of 315 and 415 square mm (respectively) to accommodate such expandable prosthetic heart valves. In that several embodiments of annuloplasty rings herein are generally circular in shape after dilation, the post-dilation native valve orifice will generally be circular and require diameters of about 20 and 23 mm to accommodate the above-discussed Sapien™ expandable prosthetic heart valves. The dilated native valve orifice will generally be smaller than the dilated annuloplasty ring orifice area due to portions of the native valve (such as leaflets, etc) that can project inward of the annuloplasty ring.

In order to accommodate an expandable prosthetic heart valve, an annuloplasty ring according to some embodiments of the current invention will have a dilated inner orifice area that is larger by about 10%, 15%, 25%, 30%, or more than the pre-dilation inner orifice area. Where an annuloplasty ring is generally circular both prior to a after dilation, the annuloplasty ring post-dilation inner diameter may be larger by about 15%, 20%, 25%, 30%, 35%, or more than the pre-dilation inner diameter.

Note that the invention is not limited to the above differences between pre- and post-dilation inner diameters and/or orifice areas of the annuloplasty ring. For example, there may be applications where much smaller and/or much larger post-dilation inner diameters may be required. In some cases an expandable prosthetic heart valve will have an outer diameter only slightly larger than its inner diameter, so that less expansion of the native valve orifice (and accordingly of the annuloplasty ring) is required in order to accommodate the expandable prosthetic heart valve. In other cases an expandable prosthetic heart valve may have an outer diameter that is much larger than its inner diameter, so that a greater expansion of the native heart valve and associated annuloplasty ring is necessary to accommodate the expandable prosthetic heart valve. There may also be applications where it may be desirable to deploy an expandable prosthetic heart valve having a smaller or larger inner diameter than was provided by the native valve.

FIGS. 18A-18B depict a further embodiment of the invention, wherein a support frame 1170 configured for use with an annuloplasty ring (such as the ring 1150 in FIGS. 17A-17D) according to the invention. The particular support frame 1170 is generally circular (although other shapes are within the scope of the invention) and defines an inner diameter 1172a, and has a generally rigid core 1174 formed from a single core element 1176 which is bent or otherwise formed into a generally circular shape with opposing ends 1178a, 1178b which meet and connect at an overlapping section 1180 having a length 1182a. The overlapping section 1180 may include adhesive, solder, welds, mechanical connections, ratchet-like assemblies, interacting portions, etc. in order to secure the overlapping ends 1178a, 1178b together. In the particular embodiment of FIGS. 18A-18B, the overlapping section 1180 includes a sliding mechanical connection 1184 having a slot 1186 secured to one opposing end 1178a, the second opposing end 1178b having been passed through the slot 1186 to form the overlapping section 1180, and also including a spring 1188 extending from the slot 1186 to the second opposing end 1178b. The spring 1188 permits expansion and/or contraction of the support frame 1170, with the spring 1188 generally biasing the support frame 1170 toward a smaller diameter, such as the smaller inner diameter 1172a of FIG. 18A. The mechanical connection 1184 also permits the support frame 1170 to be expanded when subject to an outside force such as a dilation balloon and/or expandable prosthetic valve. When the support frame is expanded 1170, the overlapping section 1180 shortens to a smaller length 1182b, and the inner diameter increases to a larger inner diameter 1172b as depicted in FIG. 18B. Note that the spring 1188 can also permit the support frame 1170 (and associated annuloplasty ring) to move with physiological annular dynamic motion, e.g., to make smaller expansions and/or contractions in response to normal valve function/heart movement as the patient's heart beats and pumps blood through the valve. The support frame 1170 may include a covering (not shown) around the core 1174, with the covering providing a surface through which suture can be passed to secure the annuloplasty ring to the native valve annulus. The support frame 1170 may be formed of various materials, including Elgiloy. The spring 1188 can be configured to provide a specific force in opposing expansion of the support frame 1170, and may be configured so that the force provided is insufficient to oppose the dilation force from a dilation balloon and/or expandable stent which might be expanded within the support frame 1170. The spring 1188 could be formed from traditional coil springs, compressible materials, pleated sewing rings, accordion sewing rings, and other configurations configured to provide a spring-like force.

Although a spring-like configuration that survives dilation is depicted in FIGS. 18A-18B, other embodiments are also within the scope of the invention. For example, a support structure may have overlapping portions having interacting portions that hold the overlapping portions together, but that will temporarily release their connection to permit the relative movement of the overlapping ends when subject to a dilation force, and then for the interacting portions to re-establish their connection once the dilation force is removed so that the support frame will again be generally rigid. Such an embodiment is generally rigid prior to dilation, becomes elastically expandable during dilation, and then becomes substantially rigid again after dilation. In a further embodiment, a support frame could be formed but with the interacting portions configured so that no fixed connection is formed between the overlapping ends after dilation, so that the support frame will be generally non-rigid after the dilation force has been applied. In such an embodiment, the support frame may be configured to provide (after dilation) an inward (compressive) force upon any expandable prosthetic valve that may be deployed within the annuloplasty ring. This inward compressive force may help to seat and otherwise hold the expandable prosthetic valve in its desired position within the native valve annulus and also within the now-dilated annuloplasty ring.

Figure 19E:
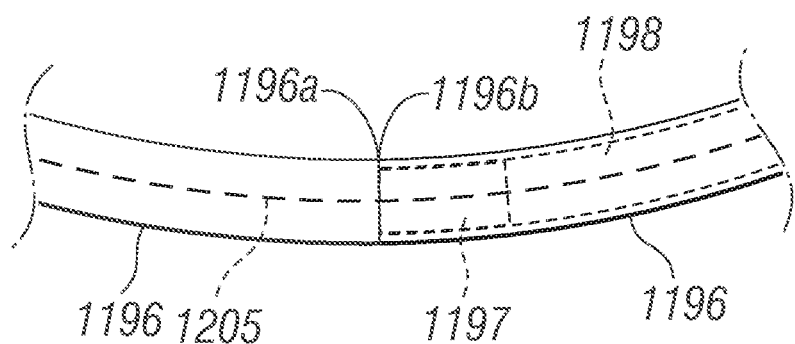
FIGS. 19E and 19F depict close-up top views, in undilated and dilated configurations, respectively, of an annuloplasty ring according to an embodiment of the invention.

In another embodiment of the invention, an annuloplasty ring includes a support frame having a rigid and/or expansion-resistant core configured to separate into a plurality of pieces when subjected to a dilation force. Such a rigid and/or expansion-resistant core could be formed as a single piece, which might include one or more weak points that are subject to separation when subjected to a dilation force. In one embodiment a rigid and/or expansion-resistant core could be formed from a plurality of segments positioned in edge-to-edge fashion and configured to separate when subjected to a dilation force. FIGS. 19A-19C depict one such embodiment of a support frame 1190 for use with a prosthetic heart valve according to the invention. The support frame 1190 is generally circular (although other shapes are within the scope of the invention) and defines an orifice 1191 having an inner diameter 1192a, and has a generally rigid and/or expansion-resistant core 1194 formed from multiple core segments 1196 which are arranged in edge-to-edge fashion to form the generally circular shape of the core 1194. Each segment 1196 has an inner lumen 1198, with the segments 1196 when assembled into the core 1194 forming a continuous core lumen 1200.

Adjacent segments 1196 join at seams 1202, which may include adhesive, solder, welds, etc. in order to secure and/or seal the seam 1202 between the adjacent segments 1196. The support frame 1190 has a pre-dilation cord 1204 and a post-dilation cord 1206 passing through the core lumen 1200. The pre-dilation cord 1204 may be a generally inelastic cord which is sufficiently tight to hold adjacent segments together and to prevent unwanted dilation of the support frame 1190. A covering (not shown) may also be included to cover the core 1194. The covering may be formed of cloth, and may be elastic.

Both the seams 1202 and pre-dilation cord 1204 are configured to fail or stretch when subjected to a dilation force, such as that provided by a dilation balloon, whereupon the support frame 1190 will assume the expanded configuration depicted in FIG. 19D, with an enlarged inner diameter 1192b. For example, the pre-dilation cord 1204 may be an inelastic cord configured to fail when subject to a selected force, such as 1, 2, 3, 4, or more atmospheres, which are within the range of forces provided by many dilation balloons used in percutaneously-deployed heart valve procedures. In one embodiment, the seams 1202 are merely sealed, with the sealant providing little if any securement against separation of adjacent segments 1196. In such an embodiment, the pre-dilation cord 1204 may serve as the sole device to hold the core segments 1196 together in the rigid and/or expansion-resistant (pre-dilation) configuration. Once the pre-dilation cord 1204 fails or stretches due to the dilation pressure, essentially all of the seams 1202 will separate so that adjacent segments 1196 separate with spaces 1208 separating the adjacent segments 1196. The remaining portions of the pre-dilation cord 1204 remain within the support frame 1190 after dilation.

The post-dilation cord 1206 remains intact after dilation and can serve to hold the support frame 1190 together post-dilation. The post-dilation cord 1206 could be elastic, and/or could be inelastic and have a larger diameter, and possibly a higher failure strength, than the pre-dilation cord 1204. If the post-dilation cord 1206 is elastic, it may provide an inward compressive force into the central orifice 1191. If the post-dilation cord 1206 is generally inelastic, it will remain intact after dilation either because its strength was too great to be ruptured by the dilation balloon or because it had a diameter that was larger than that of the inflated dilation balloon.

In a variation of the embodiment of FIGS. 19A-19D, the pre-dilation cord 1204 could be left out of the support frame 1190, and the seams 1202 themselves could have adhesive or other connections that serve to hold the segments 1196 together prior to dilation. In a further variation, the pre-dilation cord 1194 could be left out of the support frame, with a post-dilation cord 1206 configured to be elastic and with sufficient strength/elasticity to provide an inward compressive force into the central orifice with sufficient strength to hold the segments 1196 together prior to dilation, but with the inward compressive force weak enough to permit the support frame 1190 to be dilated and to permit an expandable prosthetic heart valve to be deployed therein. Accordingly, the post-dilation cord 1206 would serve as both pre-dilation cord and post-dilation cord.

Visualization references may be included on or in various portions of the device according to various embodiments of the invention. For example, visualization references may be placed on, in, or adjacent the support frame 1190, core 1194, segments 1196, pre-dilation cord 1204, and/or post-dilation cord 1206, etc. in the device of FIGS. 19A-19D. Such visualization references can help a user to properly position a dilation balloon and/or expandable prosthetic heart valve within the annuloplasty ring having the support frame 1190. For example, visualization markers positioned at the generally rigid support frame 1190 (or more specifically at the segments 1196 and/or the pre-dilation cord 1204 and/or post-dilation cord 1206) could be used to guide delivery and expansion of a dilation balloon, and also to confirm that the support frame 1190 and annuloplasty ring have been dilated. The visualization markers could also be used to guide delivery and expansion of the expandable prosthetic heart valve within the annuloplasty ring and support frame 1190, and to confirm proper deployment of the expandable prosthetic heart valve.

Figure 19F:
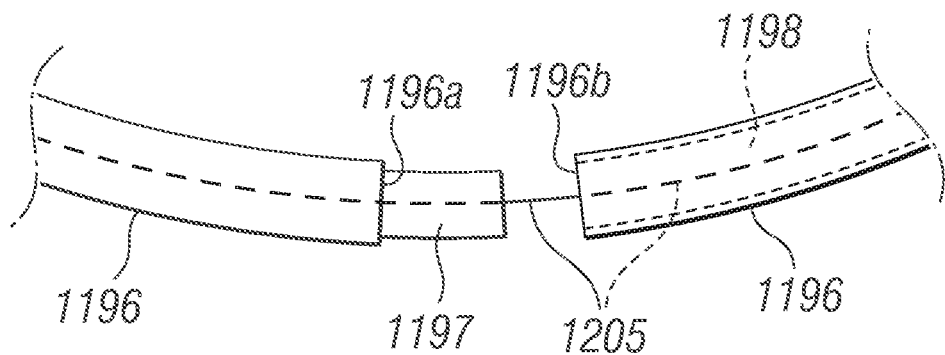

The support frame 1190 may have segments 1196 having ends 1196*a*, 1196*b* which interlock and/or otherwise interact in order to hold the segments 1196 together and/or in alignment. As depicted in the close-up view of FIG. 19E, adjacent segments 1196 may include interconnecting ends 1196*a*, 1196*b*, with one end 1196*a* having a member 1197 configured to be received within the lumen 1198 or other opening in an end 1196*b* of an adjacent segment 1196. The interconnecting ends 1196*a*, 1196*b* keep the adjacent segments 1196 in a desired alignment so that the segment ends 1196*a*, 1196*b* cannot slide sideways with respect to the member 1197 and lumen 1148, so that the general shape of the support frame 1190 is maintained. The interconnecting ends 1196*a*, 1196*b* do permit the adjacent segments 1196 to be pulled apart, as depicted in FIG. 19F, in order to permit expansion of the support frame 1190 (as was depicted in FIG. 19D). The pulling apart of the segments 1196 may be opposed by various structures set forth herein which oppose and/or restrict dilation of a support frame, such as one or more elastic and/or inelastic cords 1205 configured to oppose and/or restrict dilation of the support frame 1190 as was depicted in FIGS. 19A-19D.

Further embodiments of the invention may include an annuloplasty ring having a support frame including a core formed from segments connected end-to-end to form seams, with adjacent segments further connected via one or more individual inelastic and/or inelastic cords and elastic cords which extend only between adjacent segments. When the annuloplasty ring is subjected to a dilation force, the seams between the segments will fail and the support frame will separate into the individual segments 1172. In one particular embodiment the inelastic cords do not serve to hold adjacent segments against each other, but instead permit adjacent segments to separate when subjected to a dilation force. The inelastic cords prevent excessive separation between any adjacent segments as the dilation balloon (or other dilation force) is applied, with the result being that the segments will all be spaced generally equally apart from each other once the full dilation force is applied. After the dilation force is removed, the elastic cords will serve to pull the adjacent segments toward each other and to provide a generally inward (compressive) pressure to the valve orifice while also permitting the post-dilation inner diameter of the annuloplasty ring to be a larger size than the pre-dilation diameter.

There are many variations of the above-cited embodiments, including various combinations of the various embodiments. For example, the pre-dilation cord 1204 and/or post-dilation cord 1206 of FIGS. 19A-19D could be used with the core 1150 of FIGS. 17A-17D in order to provide inward compressive force after the core 1150 was dilated. The post-dilation cord 1206 of FIGS. 19A-19D could be replaced by a cover 1158 such as that depicted in FIGS. 17A-17D, with the cover 1158 serving to hold the post-dilation core assembly (including any segments and/or pieces thereof) together and also (if formed form elastic material) providing an inward compressive force to the orifice.

Note that, depending on the particular embodiment, an annuloplasty ring according to the invention may return to its pre-dilation inner diameter and/or shape after being subject to dilation such as from a balloon catheter. However, in such an embodiment, the balloon dilation will have rendered the "post-dilation" annuloplasty ring into a generally non-rigid and/or expansion-friendly configuration, such that a "post-dilation" annuloplasty ring will be forced with relative ease into a larger diameter and/or different shape when an expandable (e.g., balloon-expandable, self-expanding, etc.) prosthetic heart valve is deployed within the valve orifice of the native valve and annuloplasty ring.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A method of converting an annuloplasty ring in vivo, comprising:
   accessing an annuloplasty ring pre-implanted at a native annulus, the annuloplasty ring having an annuloplasty support frame defining a circumferential shape surrounding a ring opening as seen when view from above, wherein the annuloplasty support frame is configured to transition from a first configuration to a second configuration only upon being subjected to a radially expansive force in vivo of at least 1 atm, and wherein in the first configuration the ring opening is non-circular and in the second configuration the ring opening is more circular;
   inflating a dilatation balloon in vivo to apply a radially expansive force of at least 1 atm within the ring opening to cause the annuloplasty support frame to transition from the first configuration to the second configuration;
   deploying an expandable prosthetic heart valve within the annuloplasty ring in the second configuration; and expanding the prosthetic heart valve within the annuloplasty ring.

2. The method of claim 1, wherein the annuloplasty support frame has a rigid portion and a flexible portion, and the rigid portion remains unchanged in shape while the flexible portion changes shape between the first configuration and the second configuration.

3. The method of claim 2, wherein the rigid portion is curved, and the flexible portion is generally straight in the first configuration and changes shape to be curved in the second configuration.

4. The method of claim 1, wherein the annuloplasty support frame has a first rigid portion and second rigid portion shorter than and connected to the first rigid portion via a movable connection between juxtaposed ends of the rigid portions, and wherein the second rigid portion moves relative to the first rigid portion and relative to the native annulus between the first configuration and the second configuration.

5. The method of claim 4, wherein the movable connection is formed by two hinges secured between juxtaposed ends of the rigid portions configured to permit the second rigid portion to rotate relative to the first rigid portion.

6. The method of claim 4, wherein the movable connection is formed by a plastically deformable wire-like connection between juxtaposed ends of the rigid portions.

7. The method of claim 4, wherein the second rigid portion defines a curve which is directed inward with respect to the ring opening in the first configuration.

8. The method of claim 4, further including a restraint to prevent unwanted movement of the second rigid portion with respect to the first rigid portion prior to application of a radially expansive force, and the restraint is configured to release upon application of the radially expansive force.

9. The method of claim 8, wherein the restraint comprises a line of suture tied between the first rigid portion and the second rigid portion.

10. The method of claim 1, wherein the annuloplasty support frame defines a closed shape.

11. The method of claim 1, wherein the annuloplasty support frame defines an open, discontinuous shape.

12. A method of converting an annuloplasty ring in vivo, comprising:
    accessing an annuloplasty ring pre-implanted at a native annulus, the annuloplasty ring having an annuloplasty support frame defining a circumferential shape surrounding a ring opening as seen when view from above, wherein the annuloplasty support frame is configured to transition from a first configuration to a second configuration only upon being subjected to a radially expansive force, and wherein in the first configuration the ring opening is non-circular and in the second configuration the ring opening is more circular, wherein the annuloplasty support frame further has a restraint to prevent unwanted conversion from the first configuration to the second configuration prior to application of a radially expansive force;
    inflating a dilatation balloon in vivo to apply a radially expansive force within the ring opening to overcome the restraint and cause the annuloplasty support frame to transition from the first configuration to the second configuration;
    deploying an expandable prosthetic heart valve within the annuloplasty ring in the second configuration; and
    expanding the prosthetic heart valve within the annuloplasty ring.

13. The method of claim 12, wherein the annuloplasty support frame has a first rigid portion and second rigid portion shorter than and connected to the first rigid portion via a movable connection between juxtaposed ends of the rigid portions, and wherein the second rigid portion moves relative to the first rigid portion and relative to the native annulus between the first configuration and the second configuration.

14. The method of claim 13, wherein the movable connection is formed by two hinges secured between juxtaposed ends of the rigid portions configured to permit the second rigid portion to rotate relative to the first rigid portion.

15. The method of claim 13, wherein the movable connection is formed by a plastically deformable wire-like connection between juxtaposed ends of the rigid portions.

16. The method of claim 13, wherein the second rigid portion defines a curve which is directed inward with respect to the ring opening in the first configuration.

17. The method of claim 13, wherein the restraint comprises a line of suture tied between the first rigid portion and the second rigid portion.

18. The method of claim 12, wherein the annuloplasty support frame defines a closed shape.

19. The method of claim 12, wherein the annuloplasty support frame defines an open, discontinuous shape.

20. The method of claim 12, wherein the dilation balloon is configured with a pre-set inflated outer diameter which is 10-20% larger than the ring opening.

21. The method of claim 12, wherein the radially expansive force is between 1-6 atmospheres.

22. The method of claim 12, wherein in the first configuration the ring opening is "D"-shaped.

23. The method of claim 1, wherein in the first configuration the ring opening is "D"-shaped.

* * * * *